US008820257B2

(12) United States Patent
Chisholm et al.

(10) Patent No.: US 8,820,257 B2
(45) Date of Patent: Sep. 2, 2014

(54) AMPHIPHILIC FOULING RELEASE COATINGS

(75) Inventors: Bret Ja Chisholm, West Fargo, ND (US); David Allen Christianson, Bismarck, ND (US)

(73) Assignee: NDSU Research Foundation, Fargo, ND (US)

( * ) Notice: Subject to any disclaimer, the term of this patent is extended or adjusted under 35 U.S.C. 154(b) by 185 days.

(21) Appl. No.: 13/513,107

(22) PCT Filed: Dec. 3, 2010

(86) PCT No.: PCT/US2010/058968
§ 371 (c)(1),
(2), (4) Date: Jun. 27, 2012

(87) PCT Pub. No.: WO2011/069111
PCT Pub. Date: Jun. 9, 2011

(65) Prior Publication Data
US 2012/0255480 A1    Oct. 11, 2012

Related U.S. Application Data

(60) Provisional application No. 61/283,522, filed on Dec. 4, 2009.

(51) Int. Cl.
*B63H 1/16*      (2006.01)
*A01N 55/00*     (2006.01)
*C09D 183/08*    (2006.01)
*C09D 183/04*    (2006.01)

(52) U.S. Cl.
CPC .............. *A01N 55/00* (2013.01); *C09D 183/08* (2013.01); *C09D 183/04* (2013.01)
USPC ....................................... 114/67 A

(58) Field of Classification Search
USPC ....................................... 114/67 A
IPC ....................................... Y02T 70/123
See application file for complete search history.

(56) References Cited

U.S. PATENT DOCUMENTS 5,192,603 A * 3/1993 Slater et al. ................... 428/217
6,107,381 A   8/2000 Stein et al.
(Continued)

FOREIGN PATENT DOCUMENTS

WO   WO/2011/069111 A1   6/2011

OTHER PUBLICATIONS

Barrere et al., Anionic Polymerization of 1,3,5-Tris(trifluoropropylmethyl)cyclotrisiloxane ($F_3$) in Miniemulsion, Sep. 2001, *Macromolecules*, 34(21): 7276-7280. Available online on Sep. 12, 2001.

(Continued)

*Primary Examiner* — Stephen Avila
(74) *Attorney, Agent, or Firm* — Mueting, Raasch & Gebhardt, P.A.

(57) ABSTRACT

The present invention provides an amphiphilic polymeric material well-suited as a coating for marine applications, such as use as a fouling-release coating on the external surfaces of ships, particularly ship hulls. Also provided are methods of making the polymeric material and methods for using the polymeric material, as well as articles and surfaces that are coated with the polymeric material.

22 Claims, 9 Drawing Sheets

(56) References Cited

U.S. PATENT DOCUMENTS

| | | | |
|---|---|---|---|
| 6,180,249 | B1 | 1/2001 | Stein et al. |
| 6,187,447 | B1 | 2/2001 | Stein et al. |
| 6,403,105 | B1 | 6/2002 | Stein et al. |
| 7,771,833 | B2 | 8/2010 | Chisholm et al. |
| 8,349,447 | B2 | 1/2013 | Nakayama et al. |
| 2006/0194764 | A1* | 8/2006 | Kim et al. ............... 514/63 |
| 2007/0042199 | A1 | 2/2007 | Chisholm et al. |
| 2008/0181862 | A1 | 7/2008 | Chisholm et al. |
| 2009/0094954 | A1 | 4/2009 | Nakayama et al. |
| 2009/0117202 | A1* | 5/2009 | Feldman et al. ........ 424/613 |
| 2009/0221752 | A1* | 9/2009 | Dahling et al. ......... 525/104 |

OTHER PUBLICATIONS

Cassé et al., Combinatorial materials research applied to the development of new surface coatings V: Application of a spinning water jet for the semi-high throughput assessment of the attachment strength of marine fouling algae, Apr. 2007, *Biofouling*, 23(1-2):121-130. Available online on Apr. 5, 2007.

Cassé et al., Laboratory screening of coating libraries for algal adhesion, Jul. 2007, *Biofouling*, 23(3-4):267-276. Available online on Jul. 23, 2007.

Rittschof et al., Barnacle reattachment: a tool for studying barnacle adhesion, Jan. 2008, *Biofouling* 24(1):1-9. Available online on Nov. 30, 2007.

Stafslien et al., Combinatorial materials research applied to the development of new surface coatings III. Utilisation of a high-throughput multiwell plate screening method to rapidly assess bacterial biofilm retention on antifouling surfaces, Apr. 2007, *Biofouling*, 23(1-2):37-44. Available online on Apr. 5, 2007.

Stafslien et al., Combinatorial materials research applied to the development of new surface coatings IV. A high-throughput bacterial biofilm retention and retraction assay for screening fouling-release performance of coatings, Apr. 2007, *Biofouling*, 23(1-2):45-54. Available online on Apr. 5, 2007.

Stafslien et al., Combinatorial materials research applied to the development of new surface coatings VI: An automated spinning water jet apparatus for the high-throughput characterization of fouling-release marine coatings, Jul. 2007, *Rev. Sci. Instrum.*, 78(7):072204; 6 pages. Available online on Jul. 11, 2007.

Balamurugan, Reversible Protein Adsorption and Bioadhesion on Monolayers Terminated with Mixtures of Oligo(ethylene glycol) and Methyl Groups, Oct. 2005, *Journal of the American Chemical Society*, 127:14548-14549.

Balbyshev et al., Durable Hybrid Coatings, Annual Performance Report (2008), Contract No. FA8650-04-1-5045, Air Force Research Laboratory—Materials and Manufacturing Directorate, dates covered Oct. 1, 2007 to Sep. 1, 2008; report date Sep. 2008.

Balbyshev et al., Durable Hybrid Coatings, Annual Performance Report (2009), Contract No. FA8650-04-1-5045, Air Force Research Laboratory—Materials and Manufacturing Directorate, dates covered Oct. 1, 2008 to Sep. 1, 2009; report date Oct. 2009.

Chen et al., Silicone elastomers for reduced protein adsorption, May 2004, *Biomaterials* 25:2273-2282.

Chen et al., Protein repellant silicone surfaces by covalent immobilization of poly(ethylene oxide), May 2005, *Biomaterials* 26(15):2391-2399.

Chisolm et al., Durable Hybrid Coatings, Annual Performance Report, Contract No. FA8650-04-1-5045, Air Force Research Laboratory—Materials and Manufacturing Directorate, dates covered Jul. 19, 2004 to Oct. 17, 2007; report date Oct. 2007.

Doraiswamy et al., Matrix-assisted pulsed-laser evaporation of DOPA-modified poly(ethylene glycol) thin films, 2007, *Journal of Adhesion Science and Technology* 21(3-4):287-299.

Ekblad et al., Poly(ethylene glycol)-containing hydrogel surfaces for antifouling applications in marine and freshwater environments, Oct. 2008, *Biomacromolecules* 9(10): 2775-83 (published online Aug. 30, 2008).

Estarlich et al., The surface properties of some silicone and fluorosilicone coating materials immersed in seawater, 2000, *Biofouling* 16(2-4):263-275.

Finlay et al., Settlement of Ulva zoospores on patterned fluorinated and PEGylated monolayer surfaces, Jan. 2008, *Langmuir* 24(2):503-10 (published online Dec. 15, 2007).

Grunlan et al., Crosslinking of 1,9-Bis[glycidyloxypropyl]penta-(1'H,1'H,2'H,2'H-perfluoroalkylmethylsiloxane)s with α,ω-Diaminoalkanes: The Cure Behavior and Film Properties, Sep. 2004, *Journal of Applied Polymer Science* 94:203-210.

Grunlan et al., Minimally Adhesive Polymer Surfaces Prepared from Star Oligosiloxanes and Star Oligofluorosiloxanes, Apr. 2006, *Journal of Polymer Science: Part A: Polymer Chemistry* 44(8):2551-2566.

Gudipati et al., The antifouling and fouling-release performance of hyperbranched fluoropolymer (HBFP)-poly(ethylene glycol) (PEG) composite coatings evaluated by adsorption of biomacromolecules and the green fouling alga Ulva, Mar. 2005, *Langmuir* 21(7):3044-53.

Iguerb et al., Antifouling properties of poly(methyl methacrylate) films grafted with poly(ethylene glycol) monoacrylate immersed in seawater, Nov. 2008, *Langmuir* 24(21):12272-81 (published online Oct. 8, 2008).

Krishnan et al., Comparison of the fouling release properties of hydrophobic fluorinated and hydrophilic PEGylated block copolymer surfaces: attachment strength of the diatom Navicula and the green alga Ulva, May 2006, *Biomacromolecules* 7(5):1449-62.

Krishnan et al., Anti-biofouling properties of comblike block copolymers with amphiphilic side chains, May 2006, *Langmuir* 22(11):5075-86.

Lee et al., Single-molecule mechanics of mussel adhesion, Aug. 2006, *Proceedings of the National Academy of Sciences of the USA* 103(35):12999-13003.

Martinelli et al., Nanostructured films of amphiphilic fluorinated block copolymers for fouling release application, Nov. 2008, *Langmuir* 24(22):13138-47 (published online Oct. 17, 2008).

Murthy et al., Protein-resistant silicones: incorporation of poly(ethylene oxide) via siloxane tethers, Oct. 2007, *Biomacromolecules* 8(10):3244-52.

Murthy et al., The influence of poly(ethylene oxide) grafting via siloxane tethers on protein adsorption, May 2009, *Biomaterials* 30(13):2433-2439 (published online Feb. 15, 2009).

Statz et al., New Peptidomimetic Polymers for Antifouling Surfaces, Jun. 2005, *Journal of the American Chemical Society*, 127:7972-7973.

Statz et al., Algal antifouling and fouling-release properties of metal surfaces coated with a polymer inspired by marine mussels, 2006, *Biofouling* 22(6):391-99.

Ten Cate et al., High density hydrophilic and hydrophobic brush coatings using a polymeric primer layer, Feb. 2009, *Progress in Organic Coatings* 64:221-224 (published online Nov. 17, 2008).

Webster et al., Approaches to robust coatings with amphiphilic surfaces via self-stratification, Jul. 7, 2011, *Polymer Preprints* 52(2):1032-33.

Wyszogrodzka et al., Synthesis and characterization of glycerol dendrons, self-assembled monolayers on gold: a detailed study of their protein resistance, published online Apr. 7, 2009, *Biomacromolecules*, 10(5):1043-54.

Youngblood et al., Coatings based on side-chain ether-linked poly(ethylene glycol) and fluorocarbon polymers for the control of marine biofouling, Apr. 2003, *Biofouling* 19(Supp):91-98.

Zelisko et al., The interaction of proteins with functionalized silicones, 2004, *Polymer Preprints* 45(1):604-605.

International Preliminary Report on Patentability (Form PCT/IB/373) issued Jun. 5, 2012, in connection with International Patent Application No. PCT/US10/58968, filed Dec. 3, 2010. (2 pgs.).

International Search Report (Form PCT/ISA/210) mailed Apr. 19, 2011, in connection with International Patent Application No. PCT/US10/58968, filed Dec. 3, 2010. (4 pgs.).

Written Opinion of the International Searching Authority (Form PCT/ISA/237) mailed Apr. 19, 2011, in connection with International Patent Application No. PCT/US10/58968, filed Dec. 3, 2010. (5 pgs.).

\* cited by examiner

AMPHIPHILIC FOULING RELEASE COATINGS

This application is the §371 U.S. National Stage of International Application No. PCT/US2010/058968, filed Dec. 3, 2010, which claims the benefit of U.S. Provisional Application Ser. No. 61/283,522, filed Dec. 4, 2009, each of which is incorporated herein by reference in its entirety.

STATEMENT OF GOVERNMENT RIGHTS

This invention was made with government support under grants from the Office of Naval Research, Grant Nos. N00014-07-1-1099 and N00014-08-1-1149. The U.S. Government has certain rights in this invention.

BACKGROUND OF THE INVENTION

Fouling of surfaces exposed to an aquatic environment is a serious problem. For example, surfaces of ships such as the hull, offshore marine structures such as oil rigs, sea water conduit systems for seaside plants, buoys, heat exchangers, cooling towers, desalination equipment, filtration membranes, docks, and the like may all experience some degree of fouling when continually exposed to water. In the case of ships, fouling can inhibit vessel performance and capabilities. For example, fouling may substantially increase fuel consumption and may necessitate extensive and more frequent maintenance, all of which raise the overall costs of operation. Fouling may also reduce ship speed, maneuverability, and range, which impede performance. On another level, attachment of regionally specific aquatic organisms on ships that traverse the world can lead to the unwanted invasion and infestation of these organisms to non-indigenous harbors. In some instances, this can have severe adverse effects on local aquatic ecosystems.

Over the years there have been numerous attempts to minimize the effect of fouling on structures exposed to an aquatic environment. For example, coatings (e.g., paints, etc.) have been developed that impede the attachment and/or growth of aquatic organisms on such structures. These coatings, commonly referred to as foul-release coatings, are typically silicone elastomers that possess a low surface energy such that the adhesion strength is relatively low and organisms can be readily removed by water jetting or moving the ship at high speed through the water. However, these coatings generally exhibit poor fouling-release of slimes. Moreover, the formulations typically include silicone oil, which eventually leaches from the coating, thereby reducing its effectiveness.

SUMMARY OF THE INVENTION

The present invention provides an amphiphilic polymeric material for use in industrial and medical applications. The polymeric material is particularly well-suited as a coating for marine applications, such as use as a fouling-release coating on the external surfaces of ships, particularly ship hulls. Also provided are methods of making the polymeric material and methods for using the polymeric material, as well as articles and surfaces that are coated with the polymeric material or that otherwise include the polymeric material of the invention.

In one aspect, the invention provides a polymeric material formed by reacting a mixture that contains at least one hydrophilic component, at least one fluorine-containing component, and at least one silanol-terminated polysiloxane. Together, these constituent components advantageously impart amphiphilic character to the resulting polymeric material. Additionally, the polymeric material can be formed without the use of silicone oil. The hydrophilic component can be a polymer or a monomer. In one embodiment, the hydrophilic component is a hydrophilic polymer such as a polyalkylene glycol. In another embodiment, the hydrophilic component is a silane-functional compound. The silane-functional hydrophilic compound optionally includes a polymeric substituent. The fluorine-containing component can be a polymer or a monomer. In one embodiment, the fluorine-containing component is a silane-functional compound. The silane-functional fluorine-containing compound optionally includes a polymeric substituent. Silane-functional components optionally include an alkoxy group (e.g., they can be alkoxysilanes) which advantageously permits them to also function as crosslinking agents in the reaction mixture. The silanol-terminated polysiloxane can be a homopolymer, heteropolymer or copolymer, for example a block copolymer or a random copolymer. An exemplary silanol-terminated polysiloxane is silanol-terminated polydimethlylsiloxane.

The fluorine-containing component, hydrophilic component, and silanol-terminated polysiloxane can be separate components of the reaction mixture. Alternatively, any two of these constituents can constitute a single, bifunctional component. For example, a hydrophilic component and a fluorine-containing component can be constituents of a single, bifunctional copolymer. Likewise, at least one of the fluorine-containing component and the hydrophilic component can be part of a silanol-terminated polysiloxane.

The invention further provides fouling-release coatings, oils, films, and surface treatments formed from the polymeric material of the invention. Also provided are coated materials and surfaces, such as a substrate having a surface coated with a fouling-release coating that includes a polymeric material as described herein. Also provided are coated articles and objects, such as a maritime vessel coated with a fouling-release coating that includes a polymeric material as described herein.

In another aspect, the invention provides a method for making a polymeric material of that includes reacting at least one hydrophilic component, at least one fluorine-containing component, and at least one silanol-terminated polysiloxane under conditions to yield a polymeric material. Optionally, the method includes adding a crosslinking agent to react with the at least one hydrophilic component, at least one fluorine-containing component, and at least one silanol-terminated polysiloxane. The method further optionally includes the addition of a catalyst. The method can be carried out as a moisture cure process.

In another aspect, the invention provides a method for making a polymeric material that includes reacting at least one hydride- or vinyl-functionalized first component, at least one hydride- or vinyl-functionalized second component, and a hydride- or vinyl-functionalized silanol-terminated polysiloxane, wherein at least one of the first and second components comprises a hydrophilic group and at least one of the first and second components comprises a fluorine-containing group, under conditions to yield a polymeric material. The method can be carried out as an addition cure process.

In yet another aspect, the invention provides method for making a functionalized siloxane that includes reacting at least one hydride- or vinyl-functionalized first component, at least one hydride- or vinyl-functionalized second component, and a vinyl- or hydride-functionalized polysiloxane, wherein at least one of the first and second components includes a hydrophilic group and at least one of the first and second components includes a fluorine-containing group, under conditions to yield a functionalized siloxane. The functionalized siloxane can be a cyclic siloxane. A silanol-terminated polysiloxane can be formed by subjecting the functionalized cyclic siloxane to anionic ring-opening miniemulsion polymerization under conditions to yield a silanol-terminated polysiloxane. Advantageously, the silanol-terminated polysiloxane can take the form of an amphiphilic copolymer that includes at least one hydrophilic group at least one fluorine-containing group. A polymeric material can be formed by reacting the amphiphilic silanol-terminated polysiloxane with a polysiloxane such as polydimethylsiloxane.

In another aspect, the invention provides a method for protecting the surface of a substrate or article that includes coating the surface of the substrate or article with the polymeric material described herein. The invention further provides a method for facilitating the removal of a biofilm or marine organism from a substrate or article surface (such as the surface of a vessel) that includes coating the surface with a polymeric material as described herein.

BRIEF DESCRIPTIONS OF THE DRAWINGS

Figure 6:
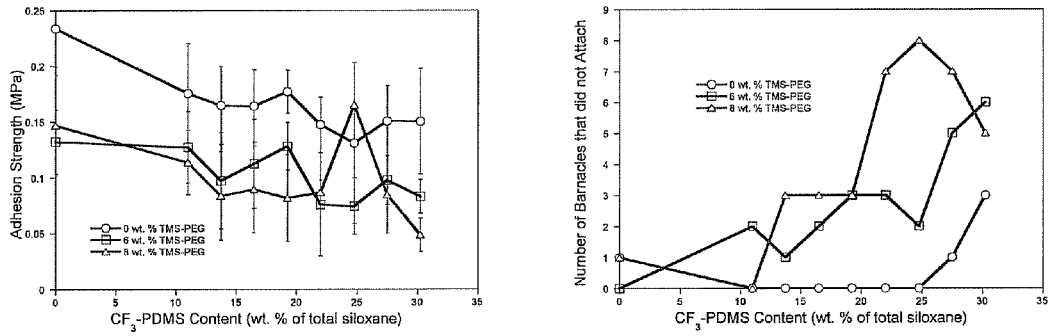

FIG. 6 shows a barnacle reattachment assay. For the assay, 10 live, adult barnacles were used for each coating. The figure to the right displays the number of barnacles that would not attach to the coating surface.

Figure 7:
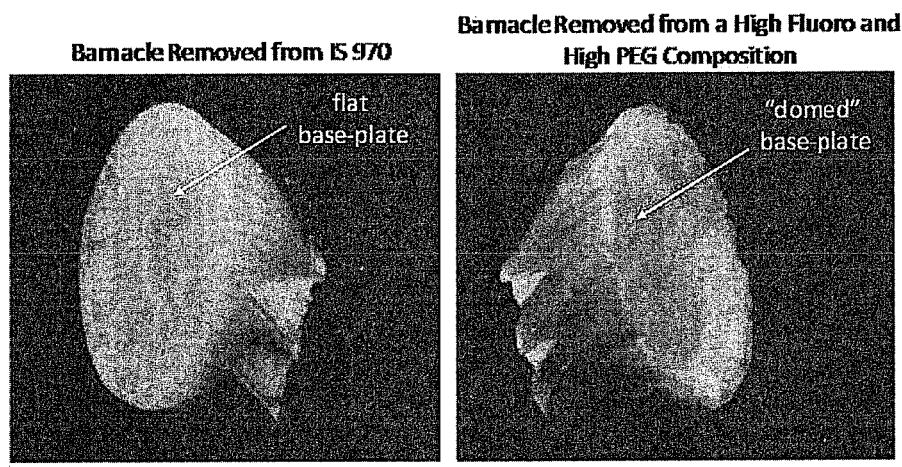

FIG. 7 shows images of a reattached barnacle removed from Intersleek 970 (IS 970) and a reattached barnacle removed from the coating containing the highest concentrations of TMS-PEG and $CF_3$-PDMS.

Figure 8:
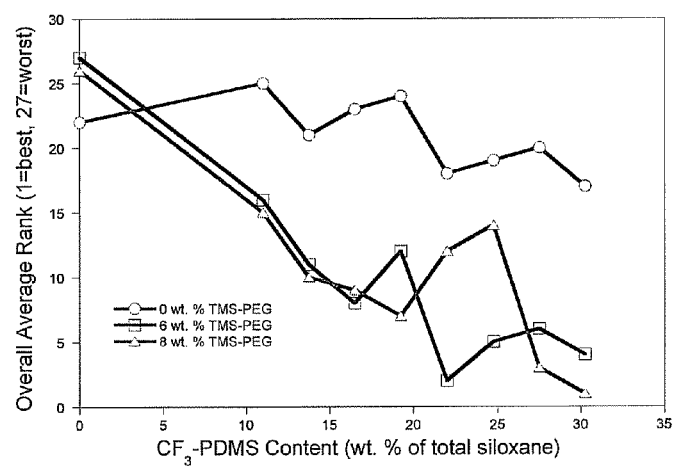

FIG. 8 shows overall average rank obtained for fouling-release measurements as a function of coating composition.

Figure 9:
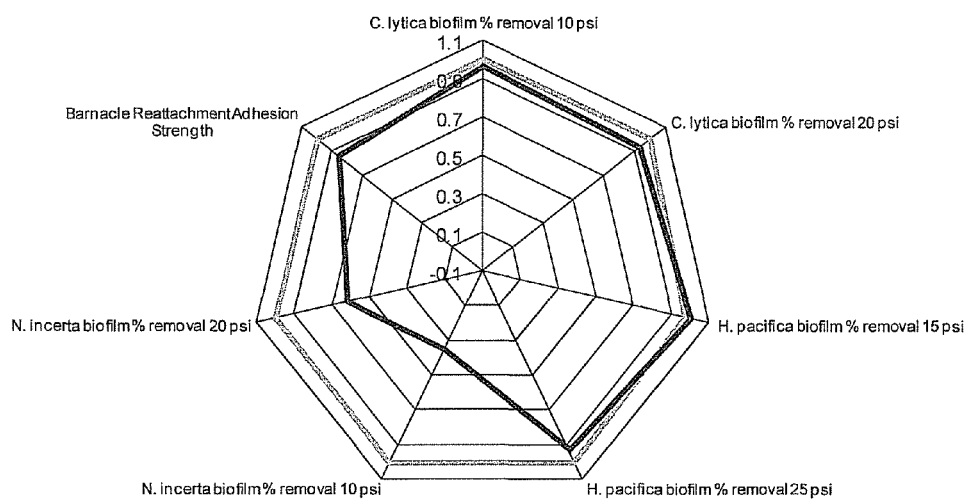

FIG. 9 shows a spider plot comparing of the experimental coating derived from the highest TMS-PEG and $CF_3$-PDMS content to Intersleek 970.

Figure 10:
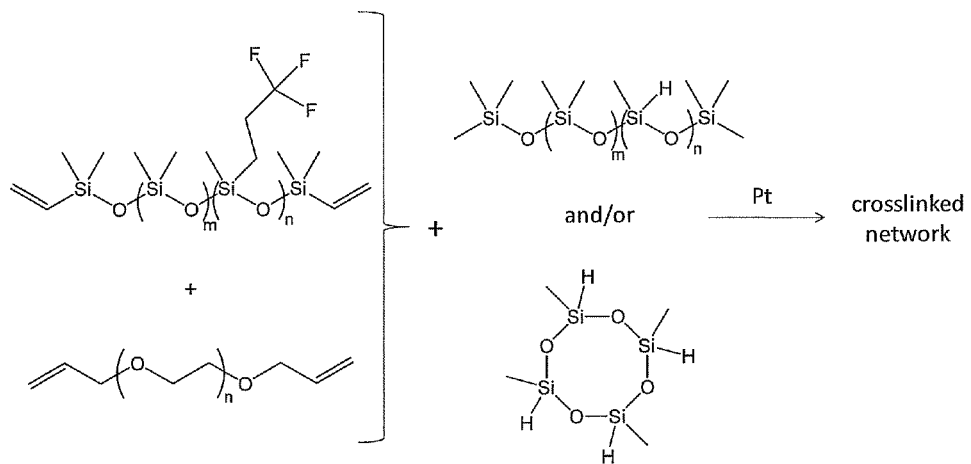

FIG. 10 shows a synthetic scheme for generating amphiphilic polysiloxane coatings using commercially-available starting materials and an addition-cure mechanism.

Figure 11:
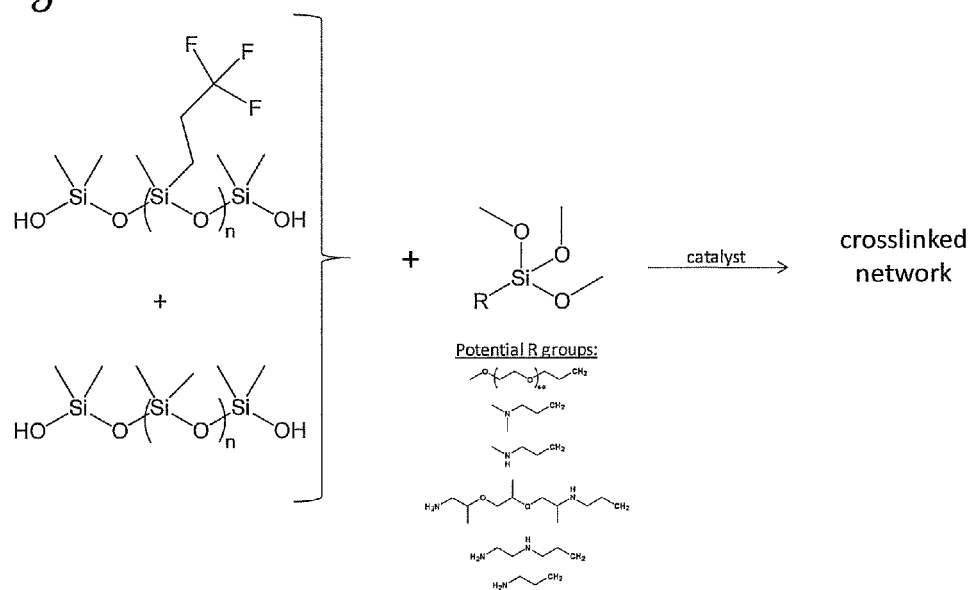

FIG. 11 shows a synthetic scheme for generating amphiphilic polysiloxane coatings using commercially-available starting materials and a moisture-cure mechanism. Hydrophilic groups are incorporated via the trimethoxysilane crosslinker.

Figure 12:
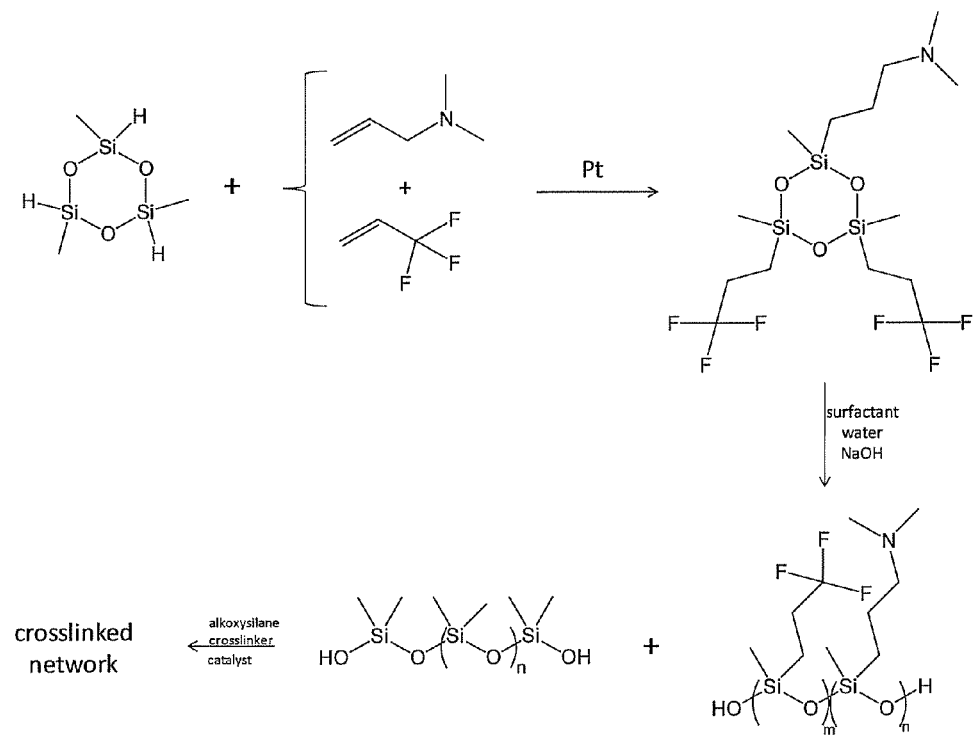

FIG. 12 shows a synthetic scheme for generating amphiphilic polysiloxane coatings using anionic ring-opening mini-emulsion polymerization (Barrere et al., Macromolecules, 2001, 34(21):7276-7280) to produce novel silanol-terminated amphiphilic polysiloxanes, followed by a moisture-cure mechanism to produce coatings.

DETAILED DESCRIPTION OF ILLUSTRATIVE EMBODIMENTS

Conventional polysiloxane fouling-release coatings provide good release of macrofoulers such as barnacles but exhibit poor fouling-release of slimes. The modified polysiloxanes of the invention show good fouling-release toward both barnacles and slimes. Also, conventional polysiloxane fouling-release coatings typically utilize a silicone oil in the formulation to enhance fouling-release properties. This silicone oil eventually leaves the coating and fouling-release performance is reduced. The modified polysiloxane coatings of the invention provide good fouling-release without the use of silicone oils which should enable long-lived fouling-release performance.

It has been found that incorporating hydrophilic moieties or segments and fluorine-containing moieties or segments into a moisture-curable polysiloxane coating results in a synergist enhancement in fouling-release properties toward a suite of marine organisms. In addition, the inclusion of the moieties does not negatively affect the mechanical properties of the coating after immersion in water.

The polymeric material of the invention is amphiphilic; that is, it contains both hydrophobic and hydrophilic moieties or segments. In a preferred embodiment, the polymeric material is formed by reacting a mixture containing at least one fluorine-containing component, at least one hydrophilic component, and at least one polysiloxane component, such as a silanol-terminated polysiloxane, under conditions to form the polymeric material. The polysiloxane component imparts hydrophobic character to the polymeric material. Amphiphilicity is incorporated into the polymeric material by either directly incorporating hydrophilic groups into a polysiloxane to yield a bifunctional amphiphilic polysiloxane, or through polymerization or cross-linking with one or more other reactive hydrophilic components. Likewise, the polymeric material is fluorine-containing by either directly incorporating fluorine atoms into a polysiloxane to yield a bifunctional fluorine-containing polysiloxane, or through polymerization or crosslinking with other reactive fluorine-containing components. In other words, and as described in more detail below, in some embodiments a fluorine-containing component and a polysiloxane component can take the form of a single component that is bifunctional; i.e., they do not need to be two separate components of the mixture. Likewise, in other embodiments, a hydrophilic component and a polysiloxane component may constitute a single component that is bifunctional. In yet other embodiments, a fluorine-containing component and a hydrophilic component may constitute a single component that is bifunctional. In yet other embodiments, two or more different fluorine-containing, hydrophilic and/or polysiloxane components may be included in the reaction mixture as desired. Regardless of how the various components are initially formulated, the resulting polymeric material is essentially a modified polysiloxane that contains both hydrophilic moieties or segments and fluorine-containing moieties or segments.

Examples of components that are useful to make the polymeric material of the invention, such as polysiloxanes, fluorine-containing components, or hydrophilic components, and reagents used to form the polymeric material, as well as examples of uses suitable for the polymeric material of the invention, are found in Chisholm et al., US Pat. Pub. 2007/0042199 published Feb. 22, 2007, now issued as U.S. Pat. No. 7,771,833, Aug. 10, 2010, and Chisholm et al., US Pat. Pub. 2008/0181862, published Jul. 31, 2008.

The polysiloxane component of the reaction mixture is preferably a silanol-terminated polysiloxane. In one embodiment, the silanol-terminated polysiloxane has an average molecular weight of at least about 5,000 g/mol. In another embodiment, the silanol terminated polysiloxane has an average molecular weight of about 10,000 g/mol to 100,000 g/mol or, suitably, about 15,000 g/mol to 75,000 g/mol. In yet another embodiment, the silanol terminated polysiloxane may have an average molecular weight of no more than about 150,000 g/mol. It should be appreciated, however, that the silanol terminated polysiloxane may have any suitable molecular weight and is not limited to any particular molecular weight or range of molecular weights described herein. The polysiloxane component can be linear, branched or cyclic. For example, the polysiloxane component can take the form of a silanol-terminated polydialkylsiloxane, a silanol-terminated polyalkylhydrosiloxane, or a silanol-terminated polysiloxane co-polymer, for example silanol-terminated polydimethylsiloxane(PDMS)-co-polymethylhydrosiloxane (PMHS).

In one embodiment, the silanol-terminated polysiloxane is a homopolymer having the general structure:

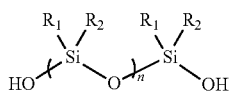

wherein $R_1$ and $R_2$ are each independently H, alkyl or aryl, provided at least one of $R_1$ and $R_2$ is alkyl or aryl, and n is about 1 to 5000, preferably about 5 to 2000. The alkyl group is preferably $(C_1-C_{10})$alkyl and can be saturated or unsaturated, linear, branched, or cyclic. Alkyl and aryl can be substituted or unsubstituted. Examples of suitable groups for incorporation into the silanol-terminated polysiloxane component as $R_1$ and/or $R_2$ include but are not limited to methyl, ethyl, phenyl, cyanopropyl, and trifluoropropyl. Silanol-terminated polydimethylsiloxane (PDMS) is an exemplary polysiloxane wherein both $R_1=R_2=$methyl; other exemplary polysiloxanes include silanol-terminated polymethylethylsiloxane, wherein $R_1=$methyl and $=R_2=$ethyl, and silanol-terminated polymethylphenylsiloxane wherein $R_1=$methyl and $R_2=$phenyl.

The polysiloxane component can alternatively be a heteropolymer that contains a plurality of different monomeric units. The pendent groups (R groups) in the heteropolymer may be the same or different, and may vary with the different monomeric units. The polysiloxane heteropolymer can take the form of a copolymer, which can be a block copolymer or a random copolymer. When formulated as a heteropolymer, at least one of the constituent monomeric units can advantageously contain a fluorine-containing or hydrophilic functionality, thereby assuming a dual role as the fluorine-containing component or the hydrophilic component of the mixture, in addition to serving as the polysiloxane component. As an example, when at least one R group is trifluoropropyl, the silanol-terminated polysiloxane may be bifunctional in that it may optionally serve as both the fluorine-containing component of the mixture and the silanol-terminated polysiloxane component. In this embodiment, the polysiloxane component can advantageously be formulated as a random or block copolymer having the structure:

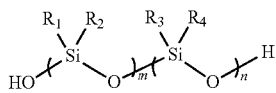

wherein $R_1$, $R_2$, $R_3$ and $R_4$ are each independently H, alkyl or aryl, provided at least one of $R_1$ and $R_2$ is alkyl or aryl and at least one $R_3$ and $R_4$ a fluorine-containing moiety, for example trifluoropropyl, and wherein m and n are each independently about 1 to 5000, more preferably 2 to 500.

The fluorine-containing component of the mixture can be either polymeric or monomeric. In one embodiment, the fluorine-containing component takes the form of a silane-functional compound, e.g., a fluorine-containing silane, preferably a fluorine-containing alkoxysilane, such as a fluorine-containing dialkoxysilane or trialkoxysilane, including but not limited to fluorine-containing di- or trimethoxysilane, di- or triethoxysilane and di- or triacetoxysilane. Essentially any reactive silane can be fluorinated to yield the fluorine-containing component of the mixture. Silazanes and chlorosilanes can also be fluorinated to yield the fluorine-containing component of the mixture.

An example of a trimethoxysilane useful as a fluorine-containing component is:

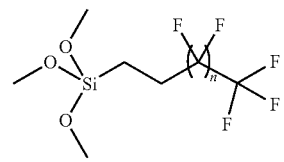

wherein n=0 to about 20.

Many other exemplary fluorine-containing alkyl compounds which are useful as fluorine-containing components of the mixture, or as functional groups that can be used to derivatize silanes or other molecules in order to produce a fluorine-containing component for use in the reaction mixture, are described in Chisholm et al., US Pat. Pub. 2007/0042199 published Feb. 22, 2007, the entirety of which is explicitly incorporated by reference.

In another embodiment, the fluorine-containing component of the mixture can take the form of a silanol-terminated fluorine-containing polysiloxane, such as silanol-terminated polytrifluoropropylmethylsiloxane ($CF_3$-PDMS). The silanol-terminated fluorine-containing polysiloxane preferably has a molecular weight of between 300 g/mol to 50,000 g/mol. Representative examples of silanol-terminated polytrifluoropropylmethylsiloxanes are shown below.

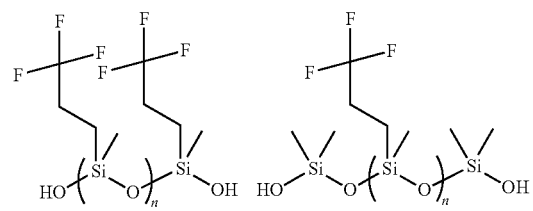

where n=1 to about 500.

In some embodiments, a fluorine-containing polysiloxane copolymer can serve as both a fluorine-containing component and a silanol-terminated polysiloxane. More particularly, when formulated as a silanol-terminated random or block copolymer of fluorine-containing monomers and non-fluorine-containing monomers, a polysiloxane copolymer can serve as both a fluorine-containing component and as a silanol-terminated polysiloxane.

The hydrophilic component of the mixture can likewise be either polymeric or monomeric. In one embodiment, the hydrophilic component has a polymeric structure and can be, for example and without limitation, a polyalkylene glycol polymer or copolymer, such as polyethylene glycol, polyacrylic acid, polyhydroxyethyl acrylate, polyacrylamide, poly(2-(dimethylamino)ethyl acrylate, polymethacrylates such as polyhydroxyethyl methacrylate, polyethacrylates, maleic anhydride copolymers, poly(ethyleneglycols), poly(ethyleneoxides), polyamines, polyimines, poly(ethyleneimine), poly(vinylamine), poly(vinyl carboxylic acid amide) and other amine-functional polymers, polyethers, polystyrenes and polystyrenesulfonate, poly(methyl vinyl ether), polyvinyl acids, and polyvinyl alcohols, as well as derivatized forms thereof. A preferred polyalkylene hydrophilic component for use in the mixture has n repeating groups, with n=1 to 100, more preferably n=4 to 25.

In another embodiment, the hydrophilic component of the reaction mixture can take the form of a silanol-terminated hydrophilic polysiloxane. A hydrophilic polysiloxane has been derivatized with a hydrophilic functional group, such as those described in more detail below, that imparts hydrophilic character to the polysiloxane. Representative examples of a silanol-terminated poly N,N-dimethylaminopropylmethylsiloxane is shown below:

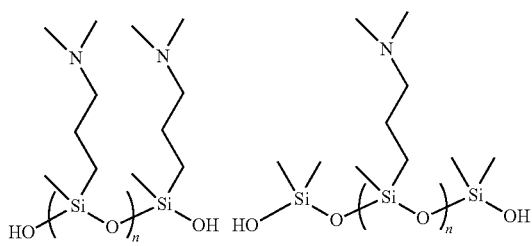

where n=1 to about 500.

A representative bifunctional copolymer, which functions as both a hydrophilic component and a fluorine-containing component, is shown as below:

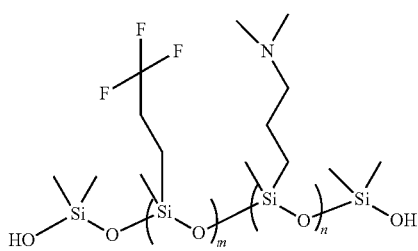

In another embodiment, the hydrophilic component of the mixture takes the form of a hydrophilic silane-functional component. A silane-functional hydrophilic component has preferably been derivatized with a functional group that imparts hydrophilic character to the silane. Silanes that can function as, or be further derivatized with one or more hydrophilic groups to function as, hydrophilic components for use in the reaction mixture include, for example, alkyoxysilanes, such as dialkoxysilanes or trialkoxysilanes, including but not limited to di- or trimethoxysilane, di- or triethoxysilane and di- or triacetoxysilane. Essentially any reactive silane can be derivatized with a hydrophilic moiety, or a repeating unit of a hydrophilic moiety, to yield a suitable hydrophilic component for use in the mixture. Silazanes and chlorosilanes can also be derivatized to yield the hydrophilic component of the mixture.

Hydrophilic functional groups that can be used to impart hydrophilicity to compounds such as silanes and polysiloxanes via covalent linkage to yield hydrophilic components suitable for use in the reaction mixture include, but not limited to, the following:

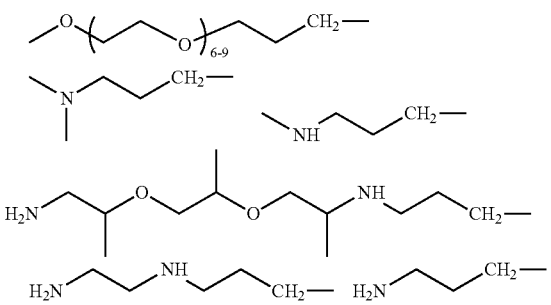

The hydrophilic functional group present on the hydrophilic component of the reaction mixture of the invention is optionally terminated with an alkoxy or hydroxy end cap group.

An example of a trimethoxysilane useful as a hydrophilic component of the reaction mixture of the invention is:

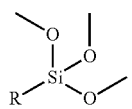

wherein the R group is a hydrophilic moiety, such as one of the functional groups described immediately above or a repeating unit of a hydrophilic moiety, such as a polyalkylene glycol, optionally terminated with an alkoxy or hydroxy end cap group.

Another exemplary trimethoxysilane useful as a hydrophilic component of the reaction mixture of the invention is one that has been functionalized by covalent attachment of a hydrophilic polymer, such as polyethylene glycol or a derivative thereof. An example is trimethoxysilane-functional PEG (TMS-PEG), i.e., 2-[methoxy(polyethyleneoxy)propyl]-trimethoxysilane, where n=1 to 20:

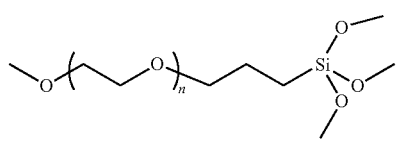

The hydrophilic component optionally includes an alkoxy group or hydroxy group. In a polymeric hydrophilic component, the alkoxy group or hydroxy group is preferably an end cap group, positioned at a terminus. Preferred terminal alkoxy groups include methoxy and ethoxy.

It will be generally appreciated that a silane-functional compound can be conveniently used for either or both of the fluorine-containing component(s) and/or the hydrophilic component(s) of the mixture. Advantageously, when formulated to contain at least one alkoxy group in addition to the fluorine-containing component(s) and/or the hydrophilic component(s), the silane-functional compound can further function as a crosslinking agent.

Generally, the silane-functional compound (as substituted silane) for use as a component in the mixture of the invention can take the form of:

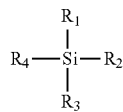

wherein, in one embodiment, at least one of $R_1$, $R_2$, $R_3$, or $R_4$ is —$OR_5$, —$NHR_6$, or halide; $R_5$ is preferably H, alkyl, aryl, or —C=$OR_6$; and $R_6$ and $R_7$ are each independently preferably H, alkyl or aryl. At least one of $R_1$, $R_2$, $R_3$, or $R_4$ is optionally H. Substituents $R_1$, $R_2$, $R_3$ and $R_4$ on the silane-functional compound can aklyl or aryl, and can independently be saturated or unsaturated, linear, branched, or cyclic; substituted or unsubstituted. In one embodiment, at least one of $R_1$, $R_2$, $R_3$ and $R_4$ is alkoxy; more preferably, at least two of $R_1$, $R_2$, $R_3$ and $R_4$ are independently be alkoxy. In a particularly preferred embodiment, at least one of $R_1$, $R_2$, $R_3$, or $R_4$ can contain a monomer, oligomer or polymer, preferably a hydrophilic monomer, oligomer or polymer, or fluorine-containing hydrophilic monomer, oligomer or polymer as described herein, and at least one, preferably two, of $R_1$, $R_2$, $R_3$, or $R_4$ are alkoxy.

The hydrophilic component(s), fluorine-containing component(s), and polysiloxane component(s) are preferably present in the mixture in the following weight percentages (wt %): hydrophilic component(s), 1 to 30 wt %, 2 to 25 wt %, or 5 to 20 wt %; fluorine-containing component(s), 3 to 80 wt %, 5 to 60 wt %, or 10-50 wt %, and the polysiloxane component(s), 0 to 80 wt %, 10 to 60 wt % or 20 to 50 wt %. Any lower limit can be combined with any upper limit to obtain a preferred range of weight percentages. It should be remembered that in some embodiments, a single component may have two functionalities (e.g., it may function as a fluorine-containing component and a polysiloxane component) and the weight percents can be adjusted accordingly.

The invention further includes a mixture containing one or more of the following reactants: one or more hydrophilic component(s) as described herein, one or more fluorine-containing component(s) as described herein, and/or one or more polysiloxane component(s) as described herein. The mixture optionally includes, either as a separate reactant or as a bifunctional component, a cross-linking agent. Also included are methods for making the polymeric material of the invention by reacting the components under conditions to foam the polymeric material. In one embodiment of the method of making a polymeric material of the invention, the reaction components are contacted with a fumed silica dispersion in butyl acetate, and a catalyst. An exemplary catalyst is tetrabutylammonium fluoride. Other exemplary catalysts include organotin compounds such as dibutyltindiacetate or dibutyltindilaurate, 1,4-diazabicyclo[2.2.2]octane, triethylamine, tetrabutylammonium hydroxide The reactants can be added in any order to form the reaction mixture. In an exemplary method, the reactants are added in the any convenient order, such as this order: fluorine-containing component, polysiloxane component, fumed silica dispersion in butyl acetate, hydrophilic component, crosslinking agent, and catalyst. The reaction mixture is stirred, preferably at ambient temperature for a time sufficient to yield the polymeric material of the invention.

Polymer cross-linking is optionally enhanced by adding a cross-linking agent to the reaction mixture. Exemplary cross-linking agents include methyltriacetoxysilane, trialkoxysilane, and tetralkoxysilane. Some compounds, including derivatized silanes such as those described above and exemplified in Example III (e.g., derivatized trimethoxysilane), can concurrently serve as both a cross-linking agent and a hydrophilic component and/or a fluorine-containing component of the reaction mixture.

It should be noted that the mixture components shown in Examples I and II are formulated to function in a process that utilizes moisture curing. One of skill in the art will note, however, that the components can be readily reformulated to function in a process that utilizes addition curing, using reaction mixture components that have been functionalized to include one or more vinyl groups and/or a hydride, preferably a silyl hydride (SiH) functionality. Thus, in another embodiment, as exemplified in Example III, FIG. 10, the invention further includes a method for making the polymeric material of the invention using an addition cure process. Any of the fluorine-containing mixture components and/or hydrophilic reaction mixture components as described herein can be functionalized to contain one or more reactive vinyl groups and/or silyl hydride (SiH) functionality. In one embodiment of the addition cure method of the invention, vinyl-functionalized fluorine-containing and/or hydrophilic components are reacted with a hydride functionalized polysiloxane component that takes the form of a linear siloxane polymer or copolymer, such as a polyalkylhydrosiloxane or a polydiakylsiloxane-co-polyalkylhydrosiloxane copolymer, or a cyclic. It should be understood that the vinyl functionality and the hydride functionality, which are both needed to participate in the addition cure reaction, can be incorporated into any of the reaction components as desired. The vinyl and hydride functionalities are typically incorporated into two or more different reaction components, but they can, if desired, be incorporated into the same component. The reaction is performed in the presence of a metal catalyst, such as platinum, to yield the polymeric material of the invention. An exemplary hydride functionalized linear siloxane copolymer contains first and second monomeric units—$SiR_1R_2$—O— and —$SiR_3R_4$—O—, respectively, wherein for the first monomer, $R_1$=$R_2$=alkyl, such as methyl; and for the second monomer, $R_3$=alkyl, such as methyl, and $R_4$=H. It should be understood that the polysiloxane component can, alternatively or additionally, contain one more vinyl functionalities. Optionally, at least one of the vinyl-functionalized or hydride functionalized fluorine-containing and/or hydrophilic polymeric components is a polymer. For example, the vinyl-functionalized fluorine-containing component can be a polysiloxane copolymer containing first and second monomeric units —$SiR_1R_2$—O— and —$SiR_3R_4$—O—, respectively, wherein for the first monomer, $R_1$=$R_2$=methyl; and for the second monomer, $R_3$=methyl and $R_4$=is a fluorine-containing group such as trifluoropropyl. An example of a suitable vinyl-functionalized hydrophilic component is vinyl-functionalized polyethylene glycol.

In another embodiment, the method of the invention can include preparation of a silanol-terminated functionalized polysiloxane copolymer using a hydrosilylation reaction, optionally followed by preparation of the polymeric material of the invention utilizing a moisture cure process; see, for example, Example III, FIG. 12. Advantageously, the hydrosilylation reaction can produce an amphiphilic polysiloxane, which can then be used as a bifunctional hydrophilic and fluorine-containing component in a moisture cure reaction to produce the polymeric material of the invention. A hydride-functionalized cyclic siloxane is reacted with at least one vinyl-functionalized reactant, which can be a vinyl-functionalized hydrophilic reactant and/or a vinyl-functionalized fluorine-containing reactant, in the presence of a metal catalyst, preferably platinum, to yield a functionalized cyclosiloxane. When at least one vinyl-functionalized hydrophilic reactant and at least one vinyl-functionalized fluorine-containing reactant are both used, the resulting functionalized cyclic siloxane is bifunctional. It should be understood that it does not matter which reactant contains the vinyl functionality and which reactant contains the hydride functionality; in other words, the reaction can occur using a vinyl-functionalized cyclic siloxane and at least one hydride-functionalized fluorine-containing reactant and/or at least one hydride-functionalized hydrophilic reactant. Examples of reactants that can be functionalized to contain a vinyl group or a hydride include compounds consisting of or containing any of the hydrophilic functional groups described herein and compounds consisting of or containing any of the fluorine-containing functional groups described herein. The derivatized cyclosiloxane intermediate is then exposed to a surfactant in the presence of an aqueous base in an anionic ring-opening reaction to yield a silanol-terminated polysiloxane oligomer or polymer. If both hydrophilic and fluorine-containing reactants were used, the product is a bifunctional silanol-terminated fluorine-containing hydrophilic polysiloxane oligomer, polymer, or copolymer. In that event, the resulting oligomer, polymer or copolymer can function as a bifunctional component, i.e., as both the fluorine-containing component and hydrophilic component, when included in the moisture cure reaction mixture of the invention. The resulting silanol-terminated oligomer, polymer or copolymer is then reacted with a polysiloxane, such as silanol-terminated polydimethylsiloxane, and optionally one or more other fluorine-containing and/or hydrophilic reaction mixture components, in the presence of a crosslinker such as an alkyoxysilane, to yield the polymeric material of the invention.

It should be understood that the invention generally includes methods for making hydrophilic component(s), fluorine-containing component(s), and polysiloxane component(s) of the mixture as described herein, as well as the hydrophilic component(s), fluorine-containing component(s), and polysiloxane component(s) thereby produced, as well methods for making the polymeric material of the invention and the polymeric material thereby produced, including methods described and exemplified in the Examples.

Methods of using the polymeric material of the invention are also included. The polymeric materials can be applied to coat or form surfaces of articles used in industrial, marine, and medical applications. Optionally a surface is treated with one or more base coats and/or one or more primer layers, in any order, prior to coating with the polymeric material of the invention.

A number of compounds suitable for use as or in anti-fouling materials are disclosed herein. In general, anti-fouling materials refer to products, agents, or compositions which may provide fouling release properties when used alone or in combination with other materials or substances. The anti-fouling materials described herein may include one or more of a number of suitable copolymers (e.g., block copolymers, graft copolymers, random copolymers, etc.) which provide fouling-release characteristics. Optionally, the polymeric material of the invention can include a functionalized polysiloxane that includes ionically or covalently bonded biocidal groups such as amines, quaternary amines, halides and the like.

The invention further contemplates preparations, formulations, coatings, films, oils, and composite materials that contain the polymeric material of the invention. Such materials are useful in many varied industrial and medical applications. Industrial applications include marine applications such as fouling-release treatments for surfaces of ships and boats such as the hull, offshore marine structures such as oil rigs, sea water conduit systems for seaside plants, buoys, heat exchangers, cooling towers, desalination equipment, filtration membranes, docks, aquatic zoo and aquarium and other structures which may all experience some degree of fouling when continually exposed to fresh or salt water. Medical applications include use as treatments for devices, including implantable devices, such as tubing, catheters, stents, vascular implants, cardiac regulation devices, and other devices that come into contact with body fluids.

Note that unless otherwise specified, "a," "an," "the," and "at least one" are used interchangeably and mean one or more than one.

Further, the present invention is illustrated by the following examples. It is to be understood that the particular examples, materials, amounts, and procedures are to be interpreted broadly in accordance with the scope and spirit of the invention as set forth herein.

EXAMPLES

Example I

Amphiphilic Siloxane Fouling-Release Coatings

We report polysiloxane coatings that contain, in addition to polysiloxane chain segments, both hydrophilic moieties such as polyethylene glycol segments and fluorine-containing moieties. The coatings provide better fouling-release properties than analogous coatings that contain, in addition to polysiloxane chain segments, only hydrophilic moieties or only fluorine-containing moieties.

Exemplary components that were tested are shown below:

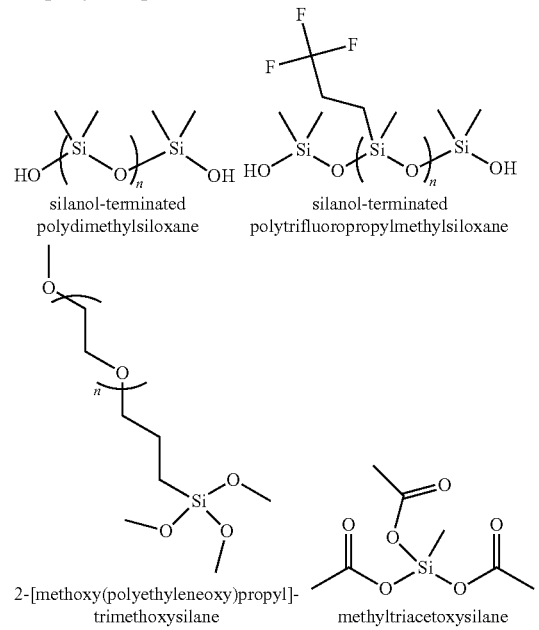

silanol-terminated polydimethylsiloxane silanol-terminated polytrifluoropropylmethylsiloxane 2-[methoxy(polyethyleneoxy)propyl]-trimethoxysilane methyltriacetoxysilane Table 1 describes the starting materials used to prepare the examples. Table 2 describes the compositions of the coating solutions prepared using an automated pipetting robot (Symx Viscous Formulation Station). Components were added in following order: FMS-9922, DMS-S35, fumed silica dispersion, butyl acetate, SIM6492.7, SIM6519.0, Catalyst solution. The coating solutions were mixed with magnetic stir bars in sealed containers at ambient conditions for approximately 16 hours. After mixing, coating specimens for evaluation of fouling-release properties were prepared by dispensing 200 microliter aliquots of coating solution into wells of a modified 24-well microtiter plate. The microtiter plate modification consisted of adhering 15 mm diameter coated aluminum discs to the bottom of the wells. The coated aluminum discs were prepared by sandblasting aluminum panels (3003 Q-panel) and then spraying International Paint Intergard 264 as a primer. From the primed aluminum panels, 15 mm discs were punched out using by a manual Unipunch press and a die. The discs were adhered to the well-bottoms of 24-well polystyrene plates (Falcon 35-1147 Sterile) with Dow Corning 734 adhesive. Next, 300 µL of a siloxane coating (Dow Corning 3140-MIL-A-46146) diluted by 50 wt. % with 4-methyl-2-pentanone was deposited into the wells to create a base coat on top of the primer layer and the base coat allowed to cure overnight.

Specimens for mechanical property testing were prepared by solution casting films onto Teflon® sheet and subsequently stamping out test specimens of the cured coating films with a dumbbell-shaped die, type D, ASTM D412-98a. Specimens for barnacle reattachment assays were prepared by coating 3"×6" aluminum panels with both the Intergard 264 primer and Dow Corning 3140-MIL-A-46146 base coat as described above and then casting five milliliters of experimental coating solution over the substrate using an adjustable 2" doctor blade with a 25 mil wet film gap setting (Symyx Technologies).

TABLE 2

Composition of Examples and Reference materials.

| Sample ID | FMS-9922 | DMS-S35 | Fumed Silica Dispersion* | butyl acetate | SIM6492.7 (90%) | SIM6519.0 | Catalyst Solution** |
|---|---|---|---|---|---|---|---|
| Reference 1 | 0 | 12.22 | 6.29 | 9.9 | 0 | 1.53 | 1.88 |
| Reference 2 | 0.51 | 11.55 | 6.29 | 9.9 | 0 | 1.53 | 1.88 |
| Reference 3 | 1.03 | 10.88 | 6.29 | 9.9 | 0 | 1.53 | 1.88 |
| Reference 4 | 1.54 | 10.21 | 6.29 | 9.9 | 0 | 1.53 | 1.88 |
| Reference 5 | 2.06 | 9.54 | 6.29 | 9.9 | 0 | 1.53 | 1.88 |
| Reference 6 | 0 | 11.95 | 6.14 | 10.02 | 0.32 | 1.49 | 1.88 |
| Example 1 | 0.5 | 11.29 | 6.14 | 10.02 | 0.32 | 1.49 | 1.88 |
| Example 2 | 1.01 | 10.63 | 6.14 | 10.02 | 0.32 | 1.49 | 1.88 |
| Example 3 | 1.51 | 9.98 | 6.14 | 10.02 | 0.32 | 1.49 | 1.88 |
| Example 4 | 2.01 | 9.32 | 6.14 | 10.02 | 0.32 | 1.49 | 1.88 |
| Reference 7 | 0 | 11.68 | 6.01 | 10.14 | 0.62 | 1.46 | 1.88 |
| Example 5 | 0.49 | 11.04 | 6.01 | 10.14 | 0.62 | 1.46 | 1.88 |
| Example 6 | 0.98 | 10.4 | 6.01 | 10.14 | 0.62 | 1.46 | 1.88 |
| Example 7 | 1.48 | 9.75 | 6.01 | 10.14 | 0.62 | 1.46 | 1.88 |
| Example 8 | 1.97 | 9.11 | 6.01 | 10.14 | 0.62 | 1.46 | 1.88 |
| Reference 8 | 0 | 11.43 | 5.87 | 10.26 | 0.91 | 1.43 | 1.88 |
| Example 9 | 0.48 | 10.8 | 5.87 | 10.26 | 0.91 | 1.43 | 1.88 |
| Example 10 | 0.96 | 10.17 | 5.87 | 10.26 | 0.91 | 1.43 | 1.88 |
| Example 11 | 1.44 | 9.54 | 5.87 | 10.26 | 0.91 | 1.43 | 1.88 |
| Example 12 | 1.92 | 8.91 | 5.87 | 10.26 | 0.91 | 1.43 | 1.88 |
| Reference 9 | 0 | 11.18 | 5.75 | 10.36 | 1.19 | 1.4 | 1.88 |
| Example 13 | 0.47 | 10.57 | 5.75 | 10.36 | 1.19 | 1.4 | 1.88 |
| Example 14 | 0.94 | 9.95 | 5.75 | 10.36 | 1.19 | 1.4 | 1.88 |
| Example 15 | 1.41 | 9.34 | 5.75 | 10.36 | 1.19 | 1.4 | 1.88 |
| Example 16 | 1.88 | 8.72 | 5.75 | 10.36 | 1.19 | 1.4 | 1.88 |

All values are in milliliters.
*Fumed silica dispersion was prepared by predispersing SIS6962.0 in butyl acetate at a 20/80 SIS6962.0/butyl acetate wt./wt. ratio.
**Catalyst Solution was prepared by dissolving 216143 in 4-methyl-2-pentanone to a final concentration of 50 mM tetrabutylammonium fluoride.

TABLE 1

Description of the starting materials used to prepare the examples.

| Tradename | Description | Manufacturer |
|---|---|---|
| FMS-9922 | Silanol terminated Polytrifluorpropylmethylsiloxane (Mw 800-1200) | Gelest |
| DMS-S35 | Silanol terminated Polydimethylsiloxane (Mw 49000) | Gelest |
| SIS6962.0 | Hexamethyldisilazane treated fumed silica | Gelest |
| SIM6519.0 | Methyltriacetoxysilane | Gelest |
| SIM6492.7 - 90% | 2-[Methoxy(Polyethyleneoxy)propyl]-trimethoxysilane (EO repeats 6-9 units) | Gelest |
| 216143 | 1M Tetrabutylammonium fluoride in Tetrahydrofuran | Aldrich |
| Butyl acetate | Butyl acetate | Aldrich |
| 4-methyl-2-pentanone | 4-methyl-2-pentanone | Alfa Aesar |

The fouling-release properties of the examples and reference coatings described by Table 2 were evaluated using a suite of biological screening assays and the data is provided in Table 3.

An automated water jet methodology was used to rapidly evaluate the adhesion of two marine bacteria, *Cellulophaga lytica* and *Halomonas pacifica*, and a microalgae diatom, *Navicula incerta*, to coatings prepared in multi-well plates (Stafslien et al., *Review of Scientific Instrum.*, 2007, 78:1-6; Casse et al., *Biofouling*, 2007, 23(2):121-130). Briefly, 24 hour cultures of the marine bacteria in marine broth were harvested via centrifugation (10,000×g for 10 minutes) and rinsed three times with sterile artificial seawater (ASW). The bacteria were then re-suspended in artificial seawater (ASW) supplemented with 0.5 g/l of peptone (*C. lytica*)/dextrose (*H. pacifica*) and 0.1 g/l of yeast extract to achieve a final cell density of $10^7$ to $10^8$ cells/ml. Three day old cultures of *N. incerta* were rinsed three times with ASW and re-suspended in Guillard's F/2 medium to achieve a final cell density of $10^5$ cells/ml. 1 ml of bacterial or microalgal suspension was added to each well of the coating plates and incubated at 28° C. for 24 hours and 18° C. for 2 hours, respectively. The plates were then transferred to the water jet apparatus and the coatings were subjected to water jet treatments at two different pressures, 10 and 20 psi for *C. lytica/N. incerta* and 15 and 25 psi for *H. pacifica*. Following water jet treatments, the coating plates containing bacteria were stained with crystal violet dye for 15 minutes, rinsed three times with ASW and imaged with a digital camera to enable percent surface coverage measurements for biofilm retraction calculations (Stafslien et al., *Biofouling*, 2007, 23(1):45-54). The crystal violet was extracted from the biofilms on the coating surfaces by adding 0.5 ml of 33% acetic acid for 15 minutes and the resulting eluates were transferred to a 96-well plate and measured for absorbance at 600 nm using a multi-well plate spectrophotometer. For the coating plates containing microalgae, the plates were imme- (>5 mm basal diameter) were dislodged from silastic T2 panels and placed on the surface of the example and control coatings. The panels were then placed in a humid container for 48 hours to facilitate initial attachment and then transferred to an ASW aquarium tank system. The reattached barnacles were fed daily with freshly hatched brine shrimp nauplii (*Artemia* sp.). After 14 days of reattachment in the aquarium system, the coatings were removed and the barnacles were dislodged with a hand-held force gauge in shear to measure the peak force at release. Once the force gauge measurements were completed, the area of the barnacle base plates were measured using a Sigma Scan Pro software package and the adhesion strengths were calculated by dividing the force required to remove the barnacles by the basal area. Barnacle adhesion for each coating was reported as the mean value of the total number of

TABLE 3

Fouling-release data obtained from the biological laboratory assays.

| Sample ID | Barnacle Reattachment (Mpa) 42 Days Water Immersion | *C lytica* Retraction % Coverage 7 days Preleach | *C lytica* Retraction % Coverage 28 days Preleach | *N. incerta* % removal 7 days Preleach | *N. incerta* % removal 28 days Preleach | *H. pacifica* % Removal 15 psi 7 days Preleach | *H. pacifica* % Removal 25 psi 7 days Preleach | *H. pacifica* % Removal 15 psi 28 days Preleach | *H. pacifica* % Removal 25 psi 28 days Preleach |
|---|---|---|---|---|---|---|---|---|---|
| Reference 1 | 0.16 ± 0.05 | 100 ± 0 | 99.3 ± 1.1 | 47.3 ± 4.5 | 53.1 ± 1.6 | 40.5 ± 2.9 | 51 ± 2.3 | 39.5 ± 2.6 | 54.2 ± 4.5 |
| Reference 2 | 0.2 ± 0.03 | 100 ± 0.1 | 71.5 ± 40.9 | 33.2 ± 5.7 | 29.1 ± 5 | 35.3 ± 7.1 | 52.4 ± 2.4 | 47.8 ± 4.3 | 54 ± 1.1 |
| Reference 3 | 0.21 ± 0.02 | 100 ± 0 | 58 ± 33.2 | 28.2 ± 1.1 | 25.8 ± 5.4 | 28.5 ± 1.3 | 56.6 ± 5 | 38.5 ± 11.4 | 39 ± 4.7 |
| Reference 4 | 0.15 ± 0.04 | 99.2 ± 0.8 | 99.5 ± 0.9 | 45.6 ± 3.8 | 24.3 ± 4.5 | 23.2 ± 1.8 | 33.4 ± 7.4 | 28.2 ± 10 | 28.5 ± 3.4 |
| Reference 5 | 0.15 ± 0.02 | 71.3 ± 2.4 | 25.5 ± 7.2 | 24.3 ± 5.1 | 16.2 ± 2.6 | 15.6 ± 2.6 | 34 ± 5.9 | 37.7 ± 5 | 53.1 ± 3.2 |
| Reference 6 | 0.13 ± 0.03 | 100 ± 0 | 90.9 ± 7.7 | 31.9 ± 6.1 | 56 ± 7.7 | 32.9 ± 4.7 | 31.8 ± 9.7 | 16.3 ± 4.6 | 29 ± 5.3 |
| Example 1 | 0.13 ± 0.04 | 25 ± 20.3 | 56.1 ± 3 | 22.7 ± 7.9 | 25.4 ± 5.8 | 19.7 ± 5 | 28.7 ± 4.1 | 21.4 ± 5.2 | 25.3 ± 7.1 |
| Example 2 | 0.17 ± 0.03 | 10.9 ± 2.6 | 19.1 ± 8.5 | 30.5 ± 11.1 | 19 ± 2.2 | 16.4 ± 3.3 | 36.8 ± 4.8 | 39.8 ± 4 | 48.8 ± 10.4 |
| Example 3 | 0.14 ± 0.04 | 5.9 ± 0.3 | 15.9 ± 1.8 | 48.2 ± 7.9 | 40.5 ± 6 | 16.6 ± 9.5 | 26 ± 10.4 | 20.6 ± 10.9 | 22.8 ± 10.5 |
| Example 4 | 0.12 ± 0.05 | 28.8 ± 4.6 | 6.3 ± 1.6 | 49.6 ± 3.2 | 14 ± 16.8 | 69.9 ± 12.4 | 85.3 ± 5.6 | 51 ± 7.1 | 63.4 ± 3.7 |
| Reference 7 | 0.11 ± 0.06 | 100 ± 0 | 100 ± 0 | 35.2 ± 2.9 | 28.8 ± 2.5 | 3.2 ± 10.7 | 11.6 ± 1.6 | 30.9 ± 37.8 | 61.5 ± 2.7 |
| Example 5 | 0.13 ± 0.02 | 10.6 ± 3.9 | 17.7 ± 3.9 | 23.3 ± 10.1 | 42 ± 6.6 | 19.2 ± 4.9 | 41.6 ± 2.4 | 32.9 ± 10.8 | 31.9 ± 2.7 |
| Example 6 | 0.12 ± 0.05 | 29.1 ± 14.4 | 24.9 ± 7 | 40.1 ± 10.3 | 37.4 ± 7 | 21.2 ± 6.8 | 33.5 ± 9.2 | 30.2 ± 5.2 | 35.3 ± 5.2 |
| Example 7 | 0.12 ± 0.03 | 16.9 ± 3 | 19 ± 5 | 49.7 ± 2.8 | 31.1 ± 12.6 | 50.5 ± 4.3 | 56.4 ± 2.4 | 36.6 ± 5.6 | 66.7 ± 9.9 |
| Example 8 | 0.11 ± 0.04 | 25.8 ± 24.6 | 1.4 ± 0.8 | 31.8 ± 13 | 45.7 ± 10.7 | 54.5 ± 12.7 | 73.8 ± 7.4 | 45.2 ± 3.5 | 50.7 ± 3.5 |
| Reference 8 | 0.12 ± 0.03 | 97.7 ± 3.9 | 99.1 ± 1.6 | 14.2 ± 3.4 | 5.5 ± 3.3 | 24.4 ± 4.2 | 33.5 ± 1.8 | 29.6 ± 4.6 | 48.4 ± 8.5 |
| Example 9 | 0.14 ± 0.03 | 50.6 ± 16 | 20.3 ± 2.2 | 62.5 ± 7.2 | 39.4 ± 9.7 | 20.8 ± 3.8 | 24.6 ± 4 | 16 ± 8.3 | 26.2 ± 3.5 |
| Example 10 | 0.10 ± 0.04 | 60.2 ± 7.6 | 14 ± 3.1 | 46.3 ± 4.2 | 28.6 ± 6.9 | 35.4 ± 3.6 | 39.7 ± 3.4 | 15.2 ± 6.8 | 28.4 ± 3.9 |
| Example 11 | 0.09 ± 0.02 | 53 ± 26 | 37.2 ± 10.3 | 53.2 ± 13.8 | 44.1 ± 6.2 | 62.5 ± 7.1 | 82.4 ± 5.5 | 53.8 ± 3.7 | 75.1 ± 0.8 |
| Example 12 | 0.13 ± 0.02 | 15.1 ± 12.4 | 5.2 ± 4.7 | 73.3 ± 2.8 | 58 ± 17.7 | 41.1 ± 9.4 | 43.2 ± 8 | 31.6 ± 15.4 | 45.3 ± 8.6 |
| Reference 9 | 0.11 ± 0.04 | 75.9 ± 17.1 | 68.2 ± 31 | 18.1 ± 6 | 29.1 ± 4.8 | 1 ± 0.1 | 24.8 ± 6.3 | 20.8 ± 8.9 | 18 ± 5.8 |
| Example 13 | 0.08 ± 0.04 | 16 ± 15.6 | 17.8 ± 12.7 | 1 ± 0.5 | 46.5 ± 7 | 21.4 ± 4.8 | 38.2 ± 2.2 | 37.2 ± 3 | 33.5 ± 17.8 |
| Example 14 | 0.12 ± 0.05 | 24.8 ± 2.5 | 22.2 ± 4.7 | 60.6 ± 15.8 | 43.3 ± 11.5 | 51.5 ± 3.1 | 50.9 ± 0.7 | 17.4 ± 14.1 | 17.3 ± 7.6 |
| Example 15 | 0.09 ± 0.05 | 28.6 ± 37.8 | 8.9 ± 9.2 | 55 ± 11.4 | 38.4 ± 7.6 | 67.5 ± 3.8 | 61.8 ± 1.7 | 36.3 ± 10 | 41.8 ± 7.8 |
| Example 16 | 0.06 ± 0.06 | 8.8 ± 0.7 | 6 ± 1.3 | 42.3 ± 10.5 | 36.9 ± 2.3 | 72.2 ± 20.3 | 102.2 ± 12.9 | 66.6 ± 10.6 | 78.8 ± 2.2 | diately extracted after water jet treatments with 1.0 ml of dimethyl sulfoxide for 15 minutes. The resulting eluates were transferred to 96-well plates and measured for fluorescence of chlorophyll (Ex: 360 nm; Em: 670 nm). Percent removal calculations were determined by comparing the total biomass on the coating surfaces before and after water jet treatments as follows:

% Removal=$(1-(TBM_J/TBM_{NJ}))\times 100$ where; $TBM_J$=mean absorbance/fluorescence value of four replicate jetted samples, $TBM_{NJ}$=mean absorbance/fluorescence value of three replicate non-jetted samples.

The coatings prepared on 3"×6" aluminium panels were evaluated for their ability to prevent or minimize the adhesion strength of barnacles using a rapid laboratory reattachment assay (Rittschof et al., *Biofouling*, 2008, 24(1):1-9). Nine adult barnacles (*Amphibalanus amphitrite*) of a testable size barnacles that had a measurable detachment force. Barnacles that had no measurable force for detachment were counted as "not attached," and not included in adhesion calculations.

To facilitate analysis of the fouling release data, Tables 5-13 were generated using the format shown in Table 4. The matrix shown in Table 4 displays variations in coating composition as a function of two components, namely, SIM6492.7 and FMS-9922. Moving from top to bottom in the matrix corresponds to a relative increase in the amount of SIM6492.7 in the coating; while moving across the matrix from left to right corresponds to an increase of FMS-9922 in the coating. The low level (0) for both components corresponds to a composition that does not contain that component. Tables 5-13 are reproductions of the matrix shown in Table 4 with the exception that the sample identification (e.g. Reference 1, Example 3, etc.) has been replaced by the average and standard deviation of a given response obtained for that sample. For example, in Table 5, the value of "25±20.3" is percent biofilm coverage obtained for "Example 1;" in Table 5, the value of "10.9±2.6" is percent biofilm coverage obtained for "Example 2;" and so on.

TABLE 4

Matrix used for analyzing fouling-release data.

| SIM6492.7 | FMS-9922 Level | | | | |
|---|---|---|---|---|---|
| Level | 0 | 1 | 2 | 3 | 4 |
| 0 | Reference 1 | Reference 2 | Reference 3 | Reference 4 | Reference 5 |
| 1 | Reference 6 | Example 1 | Example 2 | Example 3 | Example 4 |
| 2 | Reference 7 | Example 5 | Example 6 | Example 7 | Example 8 |
| 3 | Reference 8 | Example 9 | Example 10 | Example 11 | Example 12 |
| 4 | Reference 9 | Example 13 | Example 14 | Example 15 | Example 16 |

Table 5 displays the fouling-release data obtained from the bacterial biofilm retraction assay based on *C. lytica*. As described by Stafslien et al. (Stafslien et al., *Biofouling*, 2007, 23(1):45-54), this lower coating surface coverage by the biofilm corresponds to enhanced fouling-release performance. From Table 5, it can be seen that after preleaching coatings for 7 days all of the Example coatings which contained both SIM6492.7 and FMS-9922 displayed lower biofilm surface coverage (i.e. better fouling-release) than its corresponding Reference coatings that contained the same level of either SIM6492.7 or FMS-9922. For example, the surface coverage for Example 1 was lower than either Reference 2 or Reference 6; the surface coverage for Example 6 was lower than either Reference 2 or Reference 7; the surface coverage for Example 11 was lower than that of Reference 4 or Reference 8; and so on. As shown in Table 6, after preleaching the samples for 28 days, the same general result was obtained as obtained with samples preleached for 7 days.

TABLE 5

Fouling-release data obtained from the bacterial biofilm retraction assay based on *C. lytica*. Coatings were preleached for 7 days prior to testing. All values are in percent.

| SIM6492.7 | FMS-9922 Level | | | | |
|---|---|---|---|---|---|
| Level | 0 | 1 | 2 | 3 | 4 |
| 0 | 100 ± 0 | 100 ± 0.1 | 100 ± 0 | 99.2 ± 0.8 | 71.3 ± 2.4 |
| 1 | 100 ± 0 | 25 ± 20.3 | 10.9 ± 2.6 | 5.9 ± 0.3 | 28.8 ± 4.6 |
| 2 | 100 ± 0 | 10.6 ± 3.9 | 29.1 ± 14.42 | 16.9 ± 3 | 25.8 ± 24.6 |
| 3 | 97.7 ± 3.9 | 50.6 ± 16 | 60.2 ± 7.6 | 53 ± 26 | 15.1 ± 12.4 |
| 4 | 75.9 ± 17.1 | 16 ± 15.6 | 24.8 ± 2.5 | 28.6 ± 37.8 | 8.8 ± 0.7 |

TABLE 6

Fouling-release data obtained from the bacterial biofilm retraction assay based on *C. lytica*. Coatings were preleached for 21 days prior to testing. All values are in percent.

| SIM6492.7 | FMS-9922 Level | | | | |
|---|---|---|---|---|---|
| Level | 0 | 1 | 2 | 3 | 4 |
| 0 | 99.3 ± 1.1 | 71.5 ± 40.9 | 58 ± 33.2 | 99.5 ± 0.9 | 25.5 ± 7.2 |
| 1 | 90.9 ± 7.7 | 56.1 ± 3 | 19.1 ± 8.5 | 15.9 ± 1.8 | 6.3 ± 1.6 |
| 2 | 100 ± 0 | 17.7 ± 3.9 | 24.9 ± 7 | 19 ± 5 | 1.4 ± 0.8 |
| 3 | 99.1 ± 1.6 | 20.3 ± 2.2 | 14 ± 3.1 | 37.2 ± 10.3 | 5.2 ± 4.7 |
| 4 | 68.2 ± 31 | 17.8 ± 12.7 | 22.2 ± 4.7 | 8.9 ± 9.2 | 6 ± 1.3 |

Tables 7, 8, 9, and 10 display fouling-release data in matrix format for experiments conducted using the marine bacterium, *H. pacifica*. Overall, the data obtained with this assay show that, in general, Examples possessing SIM6492.7 and FMS-9922 at levels of 3 or 4 exhibit better *H. pacifica* removal than their corresponding Reference coatings that possess either SIM6492.7 or FMS-9922 at the same concentration level. Also, independent of preleach time or water-jet pressure, Examples 11 and 16 showed higher *H. pacifica* removal than any of the Reference coatings.

TABLE 7

*H. pacifica* removal data for samples preleached for 7 days. The water-jet pressure used was 15 psi. All values are in percent.

| SIM6492.7 Level | FMS-9922 Level | | | | |
|---|---|---|---|---|---|
| | 0 | 1 | 2 | 3 | 4 |
| 0 | 40.5 ± 2.9 | 35.3 ± 7.1 | 28.5 ± 1.3 | 23.2 ± 1.8 | 15.6 ± 2.6 |
| 1 | 32.9 ± 4.7 | 19.7 ± 5 | 16.4 ± 3.3 | 16.6 ± 9.5 | 69.9 ± 12.4 |
| 2 | 3.2 ± 10.7 | 19.2 ± 4.9 | 21.2 ± 6.77 | 50.5 ± 4.3 | 54.5 ± 12.7 |
| 3 | 24.4 ± 4.2 | 20.8 ± 3.8 | 35.4 ± 3.6 | 62.5 ± 7.1 | 41.1 ± 9.4 |
| 4 | 1 ± 0.1 | 21.4 ± 4.8 | 51.5 ± 3.1 | 67.5 ± 3.8 | 72.2 ± 20.3 |

TABLE 8

*H. pacifica* removal data for samples preleached for 7 days. The water-jet pressure used was 25 psi. All values are in percent.

| SIM6492.7 Level | FMS-9922 Level | | | | |
|---|---|---|---|---|---|
| | 0 | 1 | 2 | 3 | 4 |
| 0 | 51 ± 2.3 | 52.4 ± 2.4 | 56.6 ± 5 | 33.4 ± 7.4 | 34 ± 5.9 |
| 1 | 31.8 ± 9.7 | 28.7 ± 4.1 | 36.8 ± 4.8 | 26 ± 10.4 | 85.3 ± 5.6 |
| 2 | 11.6 ± 1.6 | 41.6 ± 2.4 | 33.53 ± 9.23 | 56.4 ± 2.4 | 73.8 ± 7.4 |
| 3 | 33.5 ± 1.8 | 24.6 ± 4 | 39.7 ± 3.4 | 82.4 ± 5.5 | 43.2 ± 8 |
| 4 | 24.8 ± 6.3 | 38.2 ± 2.2 | 50.9 ± 0.7 | 61.8 ± 1.7 | 102.2 ± 12.9 |

TABLE 9

*H. pacifica* removal data for samples preleached for 28 days. The water-jet pressure used was 15 psi. All values are in percent.

| SIM6492.7 Level | FMS-9922 Level | | | | |
|---|---|---|---|---|---|
| | 0 | 1 | 2 | 3 | 4 |
| 0 | 39.5 ± 2.6 | 47.8 ± 4.3 | 38.5 ± 11.4 | 28.2 ± 10 | 37.7 ± 5 |
| 1 | 16.3 ± 4.6 | 21.4 ± 5.2 | 39.8 ± 4 | 20.6 ± 10.9 | 51 ± 7.1 |
| 2 | 30.9 ± 37.8 | 32.9 ± 10.8 | 30.23 ± 5.2 | 36.6 ± 5.6 | 45.2 ± 3.5 |
| 3 | 29.6 ± 4.6 | 16 ± 8.3 | 15.2 ± 6.8 | 53.8 ± 3.7 | 31.6 ± 15.4 |
| 4 | 20.8 ± 8.9 | 37.2 ± 3 | 17.4 ± 14.1 | 36.3 ± 10 | 66.6 ± 10.6 |

TABLE 10

*H. pacifica* removal data for samples preleached for 28 days. The water-jet pressure used was 25 psi. All values are in percent.

| SIM6492.7 Level | FMS-9922 Level | | | | |
|---|---|---|---|---|---|
| | 0 | 1 | 2 | 3 | 4 |
| 0 | 54.2 ± 4.5 | 54 ± 1.1 | 39 ± 4.7 | 28.5 ± 3.4 | 53.1 ± 3.2 |
| 1 | 29 ± 5.3 | 25.3 ± 7.1 | 48.8 ± 10.4 | 22.8 ± 10.5 | 63.4 ± 3.7 |
| 2 | 61.5 ± 2.7 | 31.9 ± 2.7 | 35.28 ± 5.17 | 66.7 ± 9.9 | 50.7 ± 3.5 |
| 3 | 48.4 ± 8.5 | 26.2 ± 3.5 | 28.4 ± 3.9 | 75.1 ± 0.8 | 45.3 ± 8.6 |
| 4 | 18 ± 5.8 | 33.5 ± 17.8 | 17.3 ± 7.6 | 41.8 ± 7.8 | 78.8 ± 2.2 |

Tables 11 and 12 display fouling-release data obtained using the marine algal species, *N. incerta*. In general, the results displayed in these two tables show that Examples possessing SIM6492.7 and FMS-9922 levels of 2 or higher exhibit better *N. incerta* removal than their corresponding References that possess either SIM6492.7 or FMS-9922 at the same concentration level.

TABLE 11

Fouling-release data obtained using the marine algal species, *N. incerta*. Coatings were preleached for 7 days prior to testing. Water-jet pressure was 10 psi. All values are in percent.

| SIM6492.7 Level | FMS-9922 Level | | | | |
|---|---|---|---|---|---|
| | 0 | 1 | 2 | 3 | 4 |
| 0 | 47.3 ± 4.5 | 33.2 ± 5.7 | 28.2 ± 1.1 | 45.6 ± 3.8 | 24.3 ± 5.1 |
| 1 | 31.9 ± 6.1 | 22.7 ± 7.9 | 30.5 ± 11.1 | 48.2 ± 7.9 | 49.6 ± 3.2 |
| 2 | 35.2 ± 2.9 | 23.3 ± 10.1 | 40.1 ± 10.3 | 49.7 ± 2.8 | 31.8 ± 13 |
| 3 | 14.2 ± 3.4 | 62.5 ± 7.2 | 46.3 ± 4.2 | 53.2 ± 13.8 | 73.3 ± 2.8 |
| 4 | 18.1 ± 6 | 1 ± 0.5 | 60.6 ± 15.8 | 55 ± 11.4 | 42.3 ± 10.5 |

TABLE 12

Fouling-release data obtained using the marine algal species, *N. incerta*. Coatings were preleached for 28 days prior to testing. Water-jet pressure was 10 psi. All values are in percent.

| SIM6492.7 Level | FMS-9922 Level | | | | |
|---|---|---|---|---|---|
| | 0 | 1 | 2 | 3 | 4 |
| 0 | 53.1 ± 1.6 | 29.1 ± 5 | 25.8 ± 5.4 | 24.3 ± 4.5 | 16.2 ± 2.6 |
| 1 | 56 ± 7.7 | 25.4 ± 5.8 | 19 ± 2.2 | 40.5 ± 6 | 14 ± 16.8 |
| 2 | 28.8 ± 2.5 | 42 ± 6.6 | 37.38 ± 7.03 | 31.1 ± 12.6 | 45.7 ± 10.7 |
| 3 | 5.5 ± 3.3 | 39.4 ± 9.7 | 28.6 ± 6.9 | 44.1 ± 6.2 | 58 ± 17.7 |
| 4 | 29.1 ± 4.8 | 46.5 ± 7 | 43.3 ± 11.5 | 38.4 ± 7.6 | 36.9 ± 2.3 |

Table 13 displays results in matrix form for barnacle adhesion. In general, Examples possessing relatively high levels of both SIM6492.7 and FMS-9922 showed better barnacle removal (i.e. lower barnacle adhesion strength) than any of the References.

TABLE 13

Fouling-release data obtained using the barnacle reattachment assay. Coatings were preleached for 42 days prior to testing. All values are in MPa.

| SIM6492.7 Level | FMS-9922 Level | | | | |
|---|---|---|---|---|---|
| | 0 | 1 | 2 | 3 | 4 |
| 0 | 0.16 ± 0.05 | 0.2 ± 0.03 | 0.21 ± 0.02 | 0.15 ± 0.04 | 0.15 ± 0.02 |
| 1 | 0.13 ± 0.03 | 0.13 ± 0.04 | 0.17 ± 0.03 | 0.14 ± 0.04 | 0.12 ± 0.05 |
| 2 | 0.11 ± 0.06 | 0.13 ± 0.02 | 0.12 ± 0.05 | 0.12 ± 0.03 | 0.11 ± 0.04 |
| 3 | 0.12 ± 0.03 | 0.14 ± 0.03 | 0.1 ± 0.04 | 0.09 ± 0.02 | 0.13 ± 0.02 |
| 4 | 0.11 ± 0.04 | 0.08 ± 0.04 | 0.12 ± 0.05 | 0.09 ± 0.05 | 0.06 ± 0.06 |

The mechanical properties of coating films were determined according to ASTM 882-02 both before and after immersing in tap water for 24 hours. As shown in Table 14, in general, immersion of the Examples in water did not significantly reduce the mechanical properties.

TABLE 14

Mechanical properties of coating films before and after immersion in water.

| Sample ID | Modulus (Mpa) before immersion | Elongation before immersion | Energy to Break before immersion | Tensile Strength (Mpa) before immersion | Modulus (Mpa) after immersion | Elongation after immersion | Energy to Break after immersion | Tensile Strength (Mpa) after immersion |
|---|---|---|---|---|---|---|---|---|
| Reference 1 | 0.8 ± 0.1 | 261.9 ± 47.91 | 1.08 ± 0.37 | 1.33 ± 0.25 | 0.68 ± 0.14 | 271.67 ± 0.67 | 1.17 ± 0.55 | 1.43 ± 0.4 |
| Reference 2 | 0.61 ± 0.02 | 370.37 ± 58.02 | 2.03 ± 0.8 | 2.03 ± 0.55 | 0.57 ± 0.06 | 275.67 ± 0.3 | 1.12 ± 0.23 | 1.47 ± 0.23 |
| Reference 3 | 0.84 ± 0.08 | 290.65 ± 63.99 | 1.62 ± 0.82 | 1.9 ± 0.71 | 0.85 ± 0.04 | 324.73 ± 0.58 | 2.18 ± 0.83 | 2.37 ± 0.57 |
| Reference 4 | 0.79 ± 0.08 | 319.93 ± 108.86 | 2.01 ± 1.14 | 1.93 ± 0.74 | 0.76 ± 0.03 | 340.1 ± 0.45 | 2.22 ± 0.55 | 2.2 ± 0.3 |

TABLE 14-continued

Mechanical properties of coating films before and after immersion in water.

| Sample ID | Modulus (Mpa) before immersion | Elongation before immersion | Energy to Break before immersion | Tensile Strength (Mpa) before immersion | Modulus (Mpa) after immersion | Elongation after immersion | Energy to Break after immersion | Tensile Strength (Mpa) after immersion |
|---|---|---|---|---|---|---|---|---|
| Reference 5 | 0.69 ± 0.02 | 393.33 ± 57.41 | 2.49 ± 0.63 | 1.87 ± 0.25 | 0.75 ± 0.05 | 369.57 ± 0.46 | 2.12 ± 0.45 | 1.7 ± 0.17 |
| Reference 6 | 0.73 ± 0.04 | 338.5 ± 21.46 | 1.81 ± 0.25 | 1.9 ± 0.17 | 0.73 ± 0.02 | 262 ± 0.81 | 1.15 ± 0.61 | 1.4 ± 0.52 |
| Example 1 | 0.83 ± 0.03 | 372.73 ± 27.17 | 2.34 ± 0.3 | 2.17 ± 0.15 | 0.82 ± 0.05 | 340.13 ± 0.81 | 1.85 ± 0.83 | 1.77 ± 0.45 |
| Example 2 | 0.93 ± 0.05 | 360.27 ± 29.86 | 2.31 ± 0.3 | 2 ± 0.1 | 0.99 ± 0.09 | 372.83 ± 0.38 | 2.45 ± 0.43 | 2.07 ± 0.12 |
| Example 3 | 0.76 ± 0.04 | 362.4 ± 25 | 1.89 ± 0.25 | 1.57 ± 0.12 | 0.77 ± 0.02 | 315.17 ± 0.13 | 1.41 ± 0.1 | 1.27 ± 0.06 |
| Example 4 | 0.53 ± 0.01 | 362.73 ± 17.59 | 1.33 ± 0.14 | 1.07 ± 0.06 | 0.53 ± 0.02 | 304.63 ± 0.32 | 0.93 ± 0.15 | 0.87 ± 0.06 |
| Reference 7 | 0.79 ± 0.07 | 274.9 ± 17.61 | 1.3 ± 0.18 | 1.63 ± 0.15 | 0.84 ± 0.08 | 264.03 ± 0.66 | 1.28 ± 0.53 | 1.57 ± 0.4 |
| Example 5 | 1.04 ± 0.04 | 268.63 ± 16.67 | 1.32 ± 0.16 | 1.47 ± 0.06 | 1 ± 0.02 | 272 ± 0.06 | 1.33 ± 0.05 | 1.47 ± 0.06 |
| Example 6 | 0.99 ± 0.09 | 300.35 ± 24.79 | 1.51 ± 0.21 | 1.48 ± 0.11 | 0.97 ± 0.04 | 300.82 ± 0.14 | 1.49 ± 0.13 | 1.46 ± 0.07 |
| Example 7 | 0.89 ± 0.03 | 237.57 ± 17.42 | 0.81 ± 0.1 | 0.97 ± 0.06 | 0.86 ± 0.03 | 191.67 ± 0.19 | 0.52 ± 0.08 | 0.73 ± 0.06 |
| Example 8 | 0.46 ± 0.08 | 358.53 ± 69.97 | 1.16 ± 0.38 | 0.93 ± 0.15 | 0.53 ± 0.06 | 343.8 ± 0.92 | 1.14 ± 0.51 | 0.93 ± 0.21 |
| Reference 8 | 0.58 ± 0.04 | 340.63 ± 19.27 | 1.67 ± 0.21 | 1.73 ± 0.12 | 0.63 ± 0 | 317.73 ± 0.31 | 1.49 ± 0.35 | 1.63 ± 0.31 |
| Example 9 | 0.95 ± 0.08 | 312.5 ± 21.83 | 1.63 ± 0.2 | 1.57 ± 0.12 | 0.86 ± 0.01 | 311.1 ± 0.2 | 1.56 ± 0.18 | 1.57 ± 0.12 |
| Example 10 | 1.26 ± 0.02 | 191.9 ± 14.19 | 0.68 ± 0.09 | 0.93 ± 0.06 | 1.08 ± 0.04 | 198.2 ± 0.15 | 0.68 ± 0.08 | 0.93 ± 0.06 |
| Example 11 | 0.75 ± 0.01 | 286.13 ± 12.6 | 1.03 ± 0.09 | 1.03 ± 0.06 | 0.73 ± 0.07 | 256.07 ± 0.23 | 0.79 ± 0.12 | 0.87 ± 0.06 |
| Example 12 | 0.5 ± 0.01 | 388.67 ± 31.34 | 1.37 ± 0.22 | 1.07 ± 0.12 | 0.57 ± 0.05 | 248.67 ± 0.43 | 0.63 ± 0.17 | 0.7 ± 0.1 |
| Reference 9 | 0.82 ± 0.03 | 200.63 ± 2.9 | 0.66 ± 0.02 | 1 ± 0 | 0.89 ± 0.08 | 159.27 ± 0.02 | 0.46 ± 0.01 | 0.9 ± 0 |
| Example 13 | 1.05 ± 0.1 | 263.13 ± 24.57 | 1.22 ± 0.24 | 1.33 ± 0.15 | 1.06 ± 0.18 | 225.57 ± 0.39 | 0.89 ± 0.27 | 1.17 ± 0.21 |
| Example 14 | 0.74 ± 0.02 | 441.4 ± 8.01 | 2.45 ± 0.16 | 1.7 ± 0.1 | 0.84 ± 0.08 | 337.07 ± 0.79 | 1.61 ± 0.6 | 1.43 ± 0.29 |
| Example 15 | 0.62 ± 0.03 | 354.67 ± 47.77 | 1.42 ± 0.3 | 1.23 ± 0.12 | 0.57 ± 0.01 | 433.4 ± 0.13 | 1.99 ± 0.06 | 1.4 ± 0 |
| Example 16 | 0.61 ± 0.02 | 357.97 ± 66.22 | 1.35 ± 0.43 | 1.1 ± 0.17 | 0.7 ± 0.13 | 265.03 ± 1.16 | 0.82 ± 0.6 | 0.77 ± 0.29 |

Example II

Amphiphilic Siloxane Fouling-Release Coatings

Table 15 describes the starting materials used to prepare the examples. Table 16 describes the compositions of the coating solutions prepared using an automated pipetting robot (Symyx Viscous Formulation Station). Components were added in following order: FMS-9922, DMS-S35, fumed silica dispersion, butyl acetate, SIM6492.7, SIM6519.0, Catalyst solution. The coating solutions were mixed with magnetic stir bars in sealed containers at ambient conditions for approximately 16 hours. After mixing, coating specimens for evaluation of fouling-release properties were prepared by dispensing 200 microliter aliquots of coating solution into wells of a modified 24-well microtiter plate. The microtiter plate modification consisted of adhering 15 mm diameter coated aluminum discs to the bottom of the wells. The coated aluminum discs were prepared by sandblasting aluminum panels (3003 Q-panel) and then spraying International Paint Intergard 264 as a primer. From the primed aluminum panels, 15 mm discs were punched out using by a manual Unipunch press and a die. The discs were adhered to the well-bottoms of 24-well polystyrene plates (Falcon 35-1147 Sterile) with Dow Corning 734 adhesive. Next, 300 μL of a siloxane coating (Dow Corning 3140-MIL-A-46146) diluted by 50 wt. % with 4-methyl-2-pentanone was deposited into the wells to create a base coat on top of the primer layer and the base coat allowed to cure overnight.

Specimens for mechanical property testing were prepared by solution casting films onto Teflon® sheet and subsequently stamping out test specimens of the cured coating films with a dumbbell-shaped die, type D, ASTM D412-98a. Specimens for barnacle reattachment assays were prepared by coating 4"×8" aluminum panels with both the Intergard 264 primer and Dow Corning 3140-MIL-A-46146 base coat as described above and then casting eight milliliters of experimental coating solution over the substrate using an adjustable doctor blade with a 50 mil wet film gap setting (Paul N. Gardner Company, Inc).

TABLE 15

Description of the starting materials used to prepare the examples.

| Tradename | Description | Manufacturer |
|---|---|---|
| FMS-9922 | Silanol terminated Polytrifluorpropylmethylsiloxane (Mw 800-1200) | Gelest |
| DMS-S35 | Silanol terminated Polydimethylsiloxane (Mw 49000) | Gelest |
| SIS6962.0 | Hexamethyldisilazane treated fumed silica | Gelest |
| SIM6519.0 | Methyltriacetoxysilane | Gelest |
| SIM6492.7 - 90% | 2-[Methoxy(Polyethyleneoxy)propyl]-trimethoxysilane (EO) repeats 6-9 units) | Gelest |
| 216143 | 1M Tetrabutylammonium fluoride in Tetrahydrofuran | Aldrich |
| Butyl acetate | Butyl acetate | Aldrich |
| 4-methyl-2-pentanone | 4-methyl-2-pentanone | Alfa Aesar |

TABLE 16

Composition of Examples and Reference materials.

| Sample ID | FMS-9922 | DMS-S35 | Fumed Silica Dispersion* | butyl acetate | SIM6492.7 (90%) | SIM6519.0 | Catalyst Solution** |
|---|---|---|---|---|---|---|---|
| Reference 1 | 0 | 24.43 | 12.56 | 19.78 | 0 | 3.06 | 3.75 |
| Reference 2 | 2.06 | 21.76 | 12.57 | 19.8 | 0 | 3.06 | 3.75 |

TABLE 16-continued

Composition of Examples and Reference materials.

| Sample ID | FMS-9922 | DMS-S35 | Fumed Silica Dispersion* | butyl acetate | SIM6492.7 (90%) | SIM6519.0 | Catalyst Solution** |
|---|---|---|---|---|---|---|---|
| Reference 3 | 2.58 | 21.1 | 12.58 | 19.81 | 0 | 3.06 | 3.76 |
| Reference 4 | 3.09 | 20.42 | 12.57 | 19.81 | 0 | 3.06 | 3.75 |
| Reference 5 | 3.59 | 19.65 | 12.51 | 19.7 | 0 | 3.04 | 3.73 |
| Reference 6 | 4.11 | 19.04 | 12.55 | 19.77 | 0 | 3.05 | 3.75 |
| Reference 7 | 4.63 | 18.4 | 12.57 | 19.8 | 0 | 3.06 | 3.75 |
| Reference 8 | 6.31 | 21.74 | 15.42 | 24.29 | 0 | 3.75 | 4.6 |
| Reference 9 | 6.99 | 21.06 | 15.52 | 24.45 | 0 | 3.78 | 4.63 |
| Reference 10 | 0 | 22.95 | 11.8 | 20.6 | 1.83 | 2.87 | 3.77 |
| Example 1 | 1.93 | 20.38 | 11.78 | 20.56 | 1.83 | 2.87 | 3.76 |
| Example 2 | 2.41 | 19.75 | 11.77 | 20.55 | 1.82 | 2.86 | 3.76 |
| Example 3 | 2.9 | 19.14 | 11.79 | 20.58 | 1.83 | 2.87 | 3.76 |
| Example 4 | 3.31 | 18.14 | 11.55 | 20.17 | 1.79 | 2.81 | 3.69 |
| Example 5 | 3.88 | 17.95 | 11.83 | 20.66 | 1.83 | 2.88 | 3.78 |
| Example 6 | 4.34 | 17.25 | 11.78 | 20.57 | 1.83 | 2.87 | 3.76 |
| Example 7 | 5.92 | 20.38 | 14.45 | 25.23 | 2.24 | 3.52 | 4.62 |
| Example 8 | 6.55 | 19.74 | 14.55 | 25.4 | 2.26 | 3.54 | 4.65 |
| Reference 11 | 0 | 22.39 | 11.51 | 20.75 | 2.38 | 2.8 | 3.76 |
| Example 9 | 1.89 | 19.93 | 11.51 | 20.75 | 2.38 | 2.8 | 3.76 |
| Example 10 | 2.36 | 19.3 | 11.51 | 20.75 | 2.38 | 2.8 | 3.76 |
| Example 11 | 2.83 | 18.72 | 11.53 | 20.78 | 2.38 | 2.81 | 3.76 |
| Example 12 | 3.3 | 18.1 | 11.52 | 20.78 | 2.38 | 2.8 | 3.76 |
| Example 13 | 3.77 | 17.47 | 11.52 | 20.77 | 2.38 | 2.8 | 3.76 |
| Example 14 | 4.25 | 16.86 | 11.52 | 20.77 | 2.38 | 2.8 | 3.76 |
| Example 15 | 5.8 | 19.96 | 14.15 | 25.52 | 2.93 | 3.44 | 4.62 |
| Example 16 | 6.42 | 19.34 | 14.26 | 25.7 | 2.95 | 3.47 | 4.65 |

All values are in milliters.
*Fumed silica dispersion was prepared by predispersing SIS6962.0 in butyl acetate at a 20/80 SIS6962.0/butyl acetate wt./wt. ratio.
**Catalyst Solution was prepared by dissolving 216143 in 4-methyl-2-pentanone to a final concentration of 50 mM tetrabutylammonium fluoride.

The fouling-release properties of the examples and reference coatings described by Table 16 were evaluated using a suite of biological screening assays and the data is provided in Table 17.

An automated water jet methodology was used to rapidly evaluate the adhesion of two marine bacteria, *Cellulophaga lytica* and *Halomonas pacifica*, and a microalgae diatom, *Navicula incerta*, to coatings prepared in multi-well plates (Stafslien et al., Review of Scientific Instrum., 2007, 78:1-6; Casse et al., Biofouling, 2007, 23(2):121-130). Briefly, 24 hour cultures of the marine bacteria in marine broth were harvested via centrifugation (10,000×g for 10 minutes) and rinsed three times with sterile artificial seawater (ASW). The bacteria were then re-suspended in artificial seawater (ASW) supplemented with 0.5 g/l of peptone (*C. lytica*)/dextrose (*H. pacifica*) and 0.1 g/l of yeast extract to achieve a final cell density of $10^7$ to $10^8$ cells/ml. Three day old cultures of *N. incerta* were rinsed three times with ASW and re-suspended in Guillard's F/2 medium to achieve a final cell density of $10^5$ cells/ml. 1 ml of bacterial or microalgal suspension was added to each well of the coating plates and incubated at 28° C. for 24 hours and 18° C. for 2 hours, respectively. The plates were then transferred to the water jet apparatus and the coatings were subjected to water jet treatments at two different pressures, 10 and 20 psi for *C. lytica* and *N. incerta* and 15 and 25 psi for *H. pacifica*. Following water jet treatments, the coating plates containing bacteria were stained with crystal violet dye for 15 minutes, rinsed three times with ASW, and imaged with a digital

TABLE 17

Fouling-release data obtained from the biological laboratory assays.

| Sample ID | Barnacle Reattachment (Mpa) 28 Days Water Immersion | Barnacle Reattachment # of Non attached barnacle 28 Days Water Immersion | C lytica Retraction % Coverage 28 days Preleach | C lytica % removal 10 psi 28 days Preleach | C lytica % removal 20 psi 28 days Preleach | N. incerta % removal 10 psi 28 days Preleach | N. incerta % removal 20 psi 28 days Preleach | H. pacifica % Removal 15 psi 28 days Preleach | H. pacifica % Removal 25 psi 28 days Preleach |
|---|---|---|---|---|---|---|---|---|---|
| Reference 1 | 0.23 ± 0.03 | 1 | 100 ± 0 | 35.1 ± 7.3 | 48.1 ± 3.8 | 25 ± 12.5 | 39.3 ± 5.5 | 15.6 ± 6.7 | 6.6 ± 6.7 |
| Reference 2 | 0.18 ± 0.04 | 0 | 99.8 ± 0.3 | 46.1 ± 1.9 | 53.2 ± 1 | 4.7 ± 2.5 | 29.3 ± 3.7 | 4.8 ± 3.6 | 5.2 ± 3.9 |
| Reference 3 | 0.16 ± 0.03 | 0 | 99.9 ± 0.1 | 55 ± 2.8 | 67.1 ± 4.2 | 12.4 ± 2.2 | 32.1 ± 1 | 27.3 ± 5.9 | 20.9 ± 9.9 |
| Reference 4 | 0.16 ± 0.03 | 0 | 100 ± 0 | 40.6 ± 4.7 | 56.4 ± 3.6 | 17.4 ± 16 | 33.2 ± 4.1 | 4.6 ± 8.2 | 0 ± 15.5 |
| Reference 5 | 0.18 ± 0.02 | 0 | 99.8 ± 0.3 | 40.3 ± 1.2 | 52.6 ± 3.1 | 13.3 ± 0.3 | 38.3 ± 5.4 | 12.4 ± 5.7 | 23.3 ± 5.6 |
| Reference 6 | 0.15 ± 0.02 | 0 | 99 ± 1 | 37.9 ± 5.4 | 54.8 ± 1.5 | 18.4 ± 1.5 | 39.3 ± 7.7 | 21.9 ± 9 | 30.8 ± 10.8 |
| Reference 7 | 0.13 ± 0.07 | 0 | 88.9 ± 7.6 | 41.6 ± 2.7 | 54.3 ± 6.9 | 19.9 ± 3.2 | 35.4 ± 2 | 11.9 ± 3.1 | 15.3 ± 6.7 |
| Reference 8 | 0.15 ± 0.03 | 1 | 97.9 ± 2.9 | 45.7 ± 6.9 | 63.7 ± 0.8 | 12.2 ± 2.9 | 35.8 ± 2.6 | 12.1 ± 5.8 | 9.2 ± 4.5 |
| Reference 9 | 0.15 ± 0.05 | 3 | 93 ± 4.7 | 50.9 ± 7.7 | 67.4 ± 5.5 | 21.7 ± 3.3 | 39.2 ± 3.3 | 31.6 ± 6 | 52.4 ± 3.1 |
| Reference 10 | 0.13 ± 0.03 | 0 | 100 ± 0.1 | 36.6 ± 3.1 | 42.2 ± 11.5 | 8.9 ± 1.5 | 31.3 ± 2.6 | 15.2 ± 2.5 | 26.1 ± 5.7 |
| Example 1 | 0.13 ± 0.03 | 2 | 5.4 ± 3 | 85.6 ± 5.2 | 91.6 ± 3.2 | 24.5 ± 1.6 | 39.2 ± 7.9 | 15 ± 2.1 | 16.1 ± 6.3 |
| Example 2 | 0.1 ± 0.04 | 1 | 1.9 ± 1.3 | 93.1 ± 1.3 | 97.3 ± 1 | 33.7 ± 23.8 | 54.1 ± 11.2 | 0 ± 14.3 | 0 ± 14.3 |

TABLE 17-continued

Fouling-release data obtained from the biological laboratory assays.

| Sample ID | Barnacle Reattachment (Mpa) 28 Days Water Immersion | Barnacle Reattachment # of Non attached barnacle 28 Days Water Immersion | *C. lytica* Retraction % Coverage 28 days Preleach | *C. lytica* % removal 10 psi 28 days Preleach | *C. lytica* % removal 20 psi 28 days Preleach | *N. incerta* % removal 10 psi 28 days Preleach | *N. incerta* % removal 20 psi 28 days Preleach | *H. pacifica* % Removal 15 psi 28 days Preleach | *H. pacifica* % Removal 25 psi 28 days Preleach |
|---|---|---|---|---|---|---|---|---|---|
| Example 3 | 0.11 ± 0.04 | 2 | 4.2 ± 3.6 | 95.8 ± 0.9 | 97.3 ± 0.8 | 22.2 ± 4 | 43 ± 5.5 | 25 ± 7.2 | 33.1 ± 2.1 |
| Example 4 | 0.13 ± 0.02 | 3 | 13.5 ± 23.1 | 96.3 ± 2.8 | 99.8 ± 1.4 | 20 ± 19.9 | 39.9 ± 15.5 | 14.4 ± 7 | 15.8 ± 8.1 |
| Example 5 | 0.08 ± 0.05 | 3 | 0.1 ± 0.1 | 97.1 ± 1.8 | 98.5 ± 0.7 | 25.1 ± 11.3 | 33.4 ± 6.6 | 21.4 ± 5.2 | 41.5 ± 15.7 |
| Example 6 | 0.07 ± 0.03 | 2 | 0.8 ± 1.1 | 93.6 ± 6.9 | 94.3 ± 8.4 | 25.1 ± 15.3 | 37.9 ± 11.5 | 24.6 ± 5.2 | 29.4 ± 3.4 |
| Example 7 | 0.1 ± 0.02 | 5 | 0.5 ± 0.4 | 93.9 ± 2.3 | 94.6 ± 3.6 | 17.1 ± 6.6 | 36.2 ± 6 | 72.5 ± 0.5 | 84.8 ± 1.5 |
| Example 8 | 0.08 ± 0.02 | 6 | 2.4 ± 1.6 | 95.8 ± 2.8 | 98 ± 0.6 | 23.2 ± 5.7 | 52.4 ± 3.3 | 48.4 ± 6.7 | 49.6 ± 4.9 |
| Reference 11 | 0.15 ± 0.04 | 1 | 92.7 ± 2.5 | 30.9 ± 1.9 | 42.5 ± 1.4 | 14.3 ± 2.3 | 34.1 ± 5.4 | 0 ± 26.8 | 0 ± 26.8 |
| Example 9 | 0.11 ± 0.03 | 0 | 9.4 ± 9.6 | 94.8 ± 2 | 97.8 ± 0.7 | 23.7 ± 2.4 | 44.4 ± 6.5 | 2.1 ± 6.9 | 0 ± 7.7 |
| Example 10 | 0.08 ± 0.04 | 3 | 1.7 ± 0.1 | 96 ± 0 | 96.1 ± 3.1 | 17 ± 4.3 | 37.5 ± 8.4 | 37.1 ± 8.5 | 27.3 ± 7.2 |
| Example 11 | 0.09 ± 0.04 | 3 | 0.6 ± 0.6 | 96.7 ± 0.7 | 99.1 ± 0.5 | 18.2 ± 11.6 | 39 ± 10.7 | 8.5 ± 2.8 | 16.3 ± 3.5 |
| Example 12 | 0.08 ± 0.04 | 3 | 3.2 ± 1.1 | 95.9 ± 0.4 | 99 ± 0.4 | 15.2 ± 4 | 41.6 ± 3 | 50 ± 1.8 | 52.5 ± 6.3 |
| Example 13 | 0.09 ± 0.01 | 7 | 20 ± 10 | 94.7 ± 2 | 97.2 ± 2.1 | 16.2 ± 4.9 | 47.3 ± 0.7 | 28.4 ± 15.7 | 59.9 ± 12.4 |
| Example 14 | 0.17 * | 8 | 9.6 ± 4.5 | 92.3 ± 5.3 | 96.8 ± 2.4 | 13.1 ± 9.2 | 47.7 ± 10.7 | 57.4 ± 2.5 | 63.9 ± 4.2 |
| Example 15 | 0.08 ± 0.03 | 7 | 8.2 ± 5 | 97.3 ± 0.3 | 97 ± 0.6 | 23.3 ± 6.5 | 51.2 ± 2.9 | 87.6 ± 19 | 98.4 ± 3.6 |
| Example 16 | 0.05 ± 0.02 | 5 | 13.1 ± 2.2 | 99.6 ± 0.2 | 100 ± 0.3 | 29.9 ± 2.6 | 49.6 ± 3.1 | 80.9 ± 5.5 | 100 ± 8.3 |

* Only one measurement was acquired due to inability of barnacles to attach to these surfaces camera to enable percent surface coverage measurements for biofilm retraction calculations (Stafslien et al., *Biofouling*, 2007, 23(1):45-54). The crystal violet was extracted from the biofilms on the coating surfaces by adding 0.5 ml of 33% acetic acid for 15 minutes and the resulting eluates were transferred to a 96-well plate and measured for absorbance at 600 nm using a multi-well plate spectrophotometer. For the coating plates containing microalgae, the plates were immediately extracted after water jet treatments with 1.0 ml of dimethyl sulfoxide for 15 minutes. The resulting eluates were transferred to 96-well plates and measured for fluorescence of chlorophyll (Ex: 360 nm; Em: 670 nm). Percent removal calculations were determined by comparing the total biomass on the coating surfaces before and after water jet treatments as follows:

% Removal=$(1-(TBM_J/TBM_{NJ}))\times 100$ where; $TBM_J$=mean absorbance/fluorescence value of four replicate jetted samples, $TBM_{NJ}$=mean absorbance/fluorescence value of three replicate non-jetted samples.

The coatings prepared on 4"×8" aluminium panels were evaluated for their ability to prevent or minimize the adhesion strength of barnacles using a rapid laboratory reattachment assay (Rittschof et al., *Biofouling*, 2008, 24(1):1-9). Nine adult barnacles (*Amphibalanus amphitrite*) of a testable size (>5 mm basal diameter) were dislodged from silastic T2 panels and placed on the surface of the example and control coatings. The panels were then placed in a humid container for 48 hours to facilitate initial attachment and then transferred to an ASW aquarium tank system. The reattached barnacles were fed daily with freshly hatched brine shrimp nauplii (*Artemia* sp.). After 28 days of reattachment in the aquarium system, the coatings were removed and the barnacles were dislodged with a hand-held force gauge in shear to measure the peak force at release. Once the force gauge measurements were completed, the area of the barnacle base plates were measured using a Sigma Scan Pro software package and the adhesion strengths were calculated by dividing the force required to remove the barnacles by the basal area. Barnacle adhesion for each coating was reported as the mean value of the total number of barnacles that had a measurable detachment force. Barnacles that had no measurable force for detachment were counted as "not attached", and not included in adhesion calculations.

To facilitate analysis of the fouling release data, Tables 19-27 were generated using the format shown in Table 18. The matrix shown in Table 18 displays variations in coating composition as a function of two components, namely, SIM6492.7 and FMS-9922. Moving from top to bottom in the matrix corresponds to a relative increase in the amount of SIM6492.7 in the coating; while moving across the matrix from left to right corresponds to an increase of FMS-9922 in the coating. The low level (0) for both components corresponds to a composition that does not contain that component. Tables 19-27 are reproductions of the matrix shown in Table 18 with the exception that the sample identification (e.g. Reference 1, Example 3, etc.) has been replaced by the average and standard deviation of a given response obtained for that sample. For example, in Table 19, the value of "5.4±3" is percent biofilm coverage obtained for "Example 1;" in Table 19, the value of "1.9±1.3" is percent biofilm coverage obtained for "Example 2;" and so on.

Table 19 displays the fouling-release data obtained from the bacterial biofilm retraction assay based on *C. lytica*. As described by Stafslien et al. (Stafslien et al., *Biofouling*, 2007, 23(1):45-54), lower coating surface coverage by the biofilm corresponds to enhanced fouling-release performance. From Table 19, it can be seen that after preleaching coatings for 28 days all of the Example coatings which contained both SIM6492.7 and FMS-9922 displayed lower biofilm surface coverage (i.e. better fouling-release) than its corresponding Reference coatings that contained the same level of either SIM6492.7 or FMS-9922. For example, the surface coverage for Example 1 was lower than either Reference 2 or Reference 10; the surface coverage for Example 6 was lower than either Reference 7 or Reference 10; the surface coverage for Example 11 was lower than that of Reference 4 or Reference 11; and so on.

Table 20 displays *C. lytica* removal data using a water-jet pressure of 10 psi. From the data in Table 20, it can be seen that all of the Examples show higher removal than their corresponding Reference coatings.

Table 21 displays *C. lytica* removal data using a water-jet pressure of 20 psi. From the data in Table 21, it can be seen that all of the Examples show higher removal than their corresponding Reference coatings.

Table 22 displays *H. pacifica* removal data using a water-jet pressure of 15 psi. From the data in Table 22, it can be seen that all of the Examples possessing the highest level of SIM6492.7 and a FMS-9922 level of 2 or higher enabled more biofilm removal than their corresponding Reference coatings.

Table 23 displays *H. pacifica* removal data using a water-jet pressure of 25 psi. From the data in Table 23, it can be seen that all of the Examples possessing the highest level of SIM6492.7 and a FMS-9922 level of 2 or higher enabled more biofilm removal than their corresponding Reference coatings.

Table 24 displays *N. incerta* removal data using a water-jet pressure of 10 psi. From the data in Table 24, it can be seen that 13 of the 16 Examples enabled more cell removal than their corresponding Reference coatings.

Table 25 displays *N. incerta* removal data using a water-jet pressure of 20 psi. From the data in Table 25, it can be seen that 12 of the 16 Examples enabled more cell removal than their corresponding Reference coatings.

Table 26 displays barnacle removal data. From the data in Table 26, it can be seen that all of the Examples provide easier barnacle removal than their corresponding Reference coatings.

During execution of the barnacle reattachment assay, it was observed that many of the barnacles failed to attach to some of the coating surfaces. Table 27 shows the number of barnacles that failed to attach to the coating during the barnacle reattachment assay. As shown in Table 27, the Example coatings resulted in more instances of failed barnacle attachment than the reference coatings.

TABLE 18

Matrix used for analyzing fouling-release data.

| SIM6492.7 Level | FMS-9922 Level | | | | | | | | |
|---|---|---|---|---|---|---|---|---|---|
| | 0 | 1 | 2 | 3 | 4 | 5 | 6 | 7 | 8 |
| 0 | Reference 1 | Reference 2 | Reference 3 | Reference 4 | Reference 5 | Reference 6 | Reference 7 | Reference 8 | Reference 9 |
| 1 | Reference 10 | Example 1 | Example 2 | Example 3 | Example 4 | Example 5 | Example 6 | Example 7 | Example 8 |
| 2 | Reference 11 | Example 9 | Example 10 | Example 11 | Example 12 | Example 13 | Example 14 | Example 15 | Example 16 |

TABLE 19

Fouling-release data obtained from the bacterial biofilm retraction assay based on *C. lytica*.

| SIM6492.7 Level | FMS-9922 Level | | | | | | | | |
|---|---|---|---|---|---|---|---|---|---|
| | 0 | 1 | 2 | 3 | 4 | 5 | 6 | 7 | 8 |
| 0 | 100 ± 0 | 99.8 ± 0.3 | 99.9 ± 0.1 | 100 ± 0 | 99.8 ± 0.3 | 99 ± 1 | 88.9 ± 7.6 | 97.9 ± 2.9 | 93 ± 4.7 |
| 1 | 100 ± 0.1 | 5.4 ± 3 | 1.9 ± 1.3 | 4.2 ± 3.6 | 13.5 ± 23.1 | 0.1 ± 0.1 | 0.8 ± 1.1 | 0.5 ± 0.4 | 2.4 ± 1.6 |
| 2 | 92.7 ± 2.5 | 9.4 ± 9.6 | 1.7 ± 0.1 | 0.6 ± 0.6 | 3.2 ± 1.1 | 20 ± 10 | 9.6 ± 4.5 | 8.2 ± 5 | 13.1 ± 2.2 |

Coatings were preleached for 28 days prior to testing. All values are in percent.

TABLE 20

*C. lytica* removal data for samples preleached for 28 days.

| SIM6492.7 Level | FMS-9922 Level | | | | | | | | |
|---|---|---|---|---|---|---|---|---|---|
| | 0 | 1 | 2 | 3 | 4 | 5 | 6 | 7 | 8 |
| 0 | 35.1 ± 7.3 | 46.1 ± 1.9 | 55 ± 2.8 | 40.6 ± 4.7 | 40.3 ± 1.2 | 37.9 ± 5.4 | 41.6 ± 2.7 | 45.7 ± 6.9 | 50.9 ± 7.7 |
| 1 | 36.6 ± 3.1 | 85.6 ± 5.2 | 93.1 ± 1.3 | 95.8 ± 0.9 | 96.3 ± 2.8 | 97.1 ± 1.8 | 93.6 ± 6.9 | 93.9 ± 2.3 | 95.8 ± 2.8 |
| 2 | 30.9 ± 1.9 | 94.8 ± 2 | 96 ± 0 | 96.7 ± 0.7 | 95.9 ± 0.4 | 94.7 ± 2 | 92.3 ± 5.3 | 97.3 ± 0.3 | 99.6 ± 0.2 |

The water-jet pressure used was 10 psi. All values are in percent.

TABLE 21

*C. lytica* removal data for samples preleached for 28 days.

| SIM6492.7 Level | FMS-9922 Level | | | | | | | | |
|---|---|---|---|---|---|---|---|---|---|
| | 0 | 1 | 2 | 3 | 4 | 5 | 6 | 7 | 8 |
| 0 | 48.1 ± 3.8 | 53.2 ± 1 | 67.1 ± 4.2 | 56.4 ± 3.6 | 52.6 ± 3.1 | 54.8 ± 1.5 | 54.3 ± 6.9 | 63.7 ± 0.8 | 67.4 ± 5.5 |
| 1 | 42.2 ± 11.5 | 91.6 ± 3.2 | 97.3 ± 1 | 97.3 ± 0.8 | 99.8 ± 1.4 | 98.5 ± 0.7 | 94.3 ± 8.4 | 94.6 ± 3.6 | 98 ± 0.6 |
| 2 | 42.5 ± 1.4 | 97.8 ± 0.7 | 96.1 ± 3.1 | 99.1 ± 0.5 | 99 ± 0.4 | 97.2 ± 2.1 | 96.8 ± 2.4 | 97 ± 0.6 | 100 ± 0.3 |

The water-jet pressure used was 20 psi. All values are in percent.

TABLE 22

*H. pacifica* removal data for samples preleached for 28 days.

| SIM6492.7 | FMS-9922 Level | | | | | | | | |
|---|---|---|---|---|---|---|---|---|---|
| Level | 0 | 1 | 2 | 3 | 4 | 5 | 6 | 7 | 8 |
| 0 | 15.6 ± 6.7 | 4.8 ± 3.6 | 27.3 ± 5.9 | 4.6 ± 8.2 | 12.4 ± 5.7 | 21.9 ± 9 | 11.9 ± 3.1 | 12.1 ± 5.8 | 31.6 ± 6 |
| 1 | 15.2 ± 2.5 | 15 ± 2.1 | 0 ± 14.3 | 25 ± 7.2 | 14.4 ± 7 | 21.4 ± 5.2 | 24.6 ± 5.2 | 72.5 ± 0.5 | 48.4 ± 6.7 |
| 2 | 0 ± 26.8 | 2.1 ± 6.9 | 37.1 ± 8.5 | 8.5 ± 2.8 | 50 ± 1.8 | 28.4 ± 15.7 | 57.4 ± 2.5 | 87.6 ± 19 | 80.9 ± 5.5 |

The water-jet pressure used was 15 psi. All values are in percent.

TABLE 23

*H. pacifica* removal data for samples preleached for 28 days.

| SIM6492.7 | FMS-9922 Level | | | | | | | | |
|---|---|---|---|---|---|---|---|---|---|
| Level | 0 | 1 | 2 | 3 | 4 | 5 | 6 | 7 | 8 |
| 0 | 6.6 ± 6.7 | 5.2 ± 3.9 | 20.9 ± 9.9 | 0 ± 15.5 | 23.3 ± 5.6 | 30.8 ± 10.8 | 15.3 ± 6.7 | 9.2 ± 4.5 | 52.4 ± 3.1 |
| 1 | 26.1 ± 5.7 | 16.1 ± 6.3 | 0 ± 14.3 | 33.1 ± 2.1 | 15.8 ± 8.1 | 41.5 ± 15.7 | 29.4 ± 3.4 | 84.8 ± 1.5 | 49.6 ± 4.9 |
| 2 | 0 ± 26.8 | 0 ± 7.7 | 27.3 ± 7.2 | 16.3 ± 3.5 | 52.5 ± 6.3 | 59.9 ± 12.4 | 63.9 ± 4.2 | 98.4 ± 3.6 | 100 ± 8.3 |

The water-jet pressure used was 25 psi. All values are in percent.

TABLE 24

*N. incerta* removal data for samples preleached for 28 days.

| SIM6492.7 | FMS-9922 Level | | | | | | | | |
|---|---|---|---|---|---|---|---|---|---|
| Level | 0 | 1 | 2 | 3 | 4 | 5 | 6 | 7 | 8 |
| 0 | 25 ± 12.5 | 4.7 ± 2.5 | 12.4 ± 2.2 | 17.4 ± 16 | 13.3 ± 0.3 | 18.4 ± 1.5 | 19.9 ± 3.2 | 12.2 ± 2.9 | 21.7 ± 3.3 |
| 1 | 8.9 ± 1.5 | 24.5 ± 1.6 | 33.7 ± 23.8 | 22.2 ± 4 | 20 ± 19.9 | 25.1 ± 11.3 | 25.1 ± 15.3 | 17.1 ± 6.6 | 23.2 ± 5.7 |
| 2 | 14.3 ± 2.3 | 23.7 ± 2.4 | 17 ± 4.3 | 18.2 ± 11.6 | 15.2 ± 4 | 16.2 ± 4.9 | 13.1 ± 9.2 | 23.3 ± 6.5 | 29.9 ± 2.6 |

The water-jet pressure used was 10 psi. All values are in percent.

TABLE 25

*N. incerta* removal data for samples preleached for 28 days.

| SIM6492.7 | FMS-9922 Level | | | | | | | | |
|---|---|---|---|---|---|---|---|---|---|
| Level | 0 | 1 | 2 | 3 | 4 | 5 | 6 | 7 | 8 |
| 0 | 39.3 ± 5.5 | 29.3 ± 3.7 | 32.1 ± 1 | 33.2 ± 4.1 | 38.3 ± 5.4 | 39.3 ± 7.7 | 35.4 ± 2 | 35.8 ± 2.6 | 39.2 ± 3.3 |
| 1 | 31.3 ± 2.6 | 39.2 ± 7.9 | 54.1 ± 11.2 | 43 ± 5.5 | 39.9 ± 15.5 | 33.4 ± 6.6 | 37.9 ± 11.5 | 36.2 ± 6 | 52.4 ± 3.3 |
| 2 | 34.1 ± 5.4 | 44.4 ± 6.5 | 37.5 ± 8.4 | 39 ± 10.7 | 41.6 ± 3 | 47.3 ± 0.7 | 47.7 ± 10.7 | 51.2 ± 2.9 | 49.6 ± 3.1 |

The water-jet pressure used was 20 psi. All values are in percent.

TABLE 26

Fouling-release data obtained using the barnacle reattachment assay.

| SIM6492.7 | FMS-9922 Level | | | | | | | | |
|---|---|---|---|---|---|---|---|---|---|
| Level | 0 | 1 | 2 | 3 | 4 | 5 | 6 | 7 | 8 |
| 0 | 0.23 ± 0.03 | 0.18 ± 0.04 | 0.16 ± 0.03 | 0.16 ± 0.03 | 0.18 ± 0.02 | 0.15 ± 0.02 | 0.13 ± 0.07 | 0.15 ± 0.03 | 0.15 ± 0.05 |
| 1 | 0.13 ± 0.03 | 0.13 ± 0.03 | 0.1 ± 0.04 | 0.11 ± 0.04 | 0.13 ± 0.02 | 0.08 ± 0.05 | 0.07 ± 0.03 | 0.1 ± 0.02 | 0.08 ± 0.02 |
| 2 | 0.15 ± 0.04 | 0.11 ± 0.03 | 0.08 ± 0.04 | 0.09 ± 0.04 | 0.08 ± 0.04 | 0.09 ± 0.01 | 0.17 * | 0.08 ± 0.03 | 0.05 ± 0.02 |

* Only one measurement was acquired due to inability of barnacles to attach to these surfaces Coatings were preleached for 28 days prior to testing. All values are in MPa.

TABLE 27

Number of barnacles that failed to attach to the coating during the barnacle reattachment assay.

| SIM6492.7 | FMS-9922 Level | | | | | | | | |
|---|---|---|---|---|---|---|---|---|---|
| Level | 0 | 1 | 2 | 3 | 4 | 5 | 6 | 7 | 8 |
| 0 | | 1 | 0 | 0 | 0 | 0 | 0 | 0 | 1 | 3 |
| 1 | | 0 | 2 | 1 | 2 | 3 | 3 | 2 | 5 | 6 |
| 2 | | 1 | 0 | 3 | 3 | 3 | 7 | 8 | 7 | 5 |

Coatings were preleached for 28 days prior to testing. All values are number of non-attached barnacles out of nine total.

Figure 1:
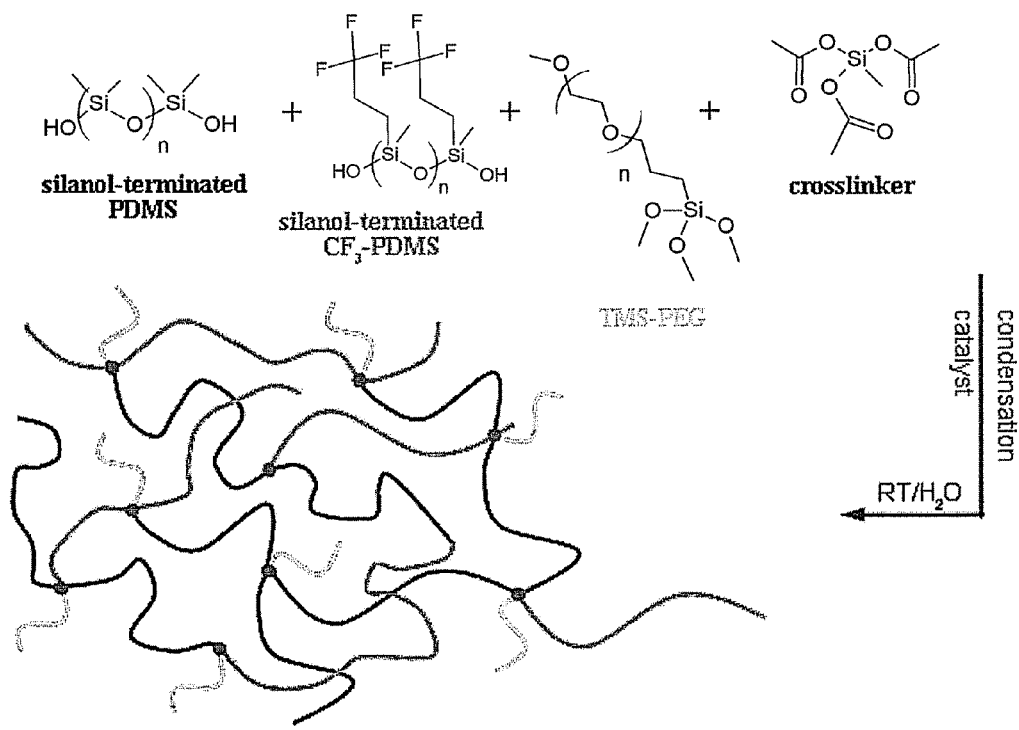
FIG. 1 shows a general compositional space that is being investigated for the production of novel fouling-release coatings based the generation of amphiphilic surfaces.
Figure 2:
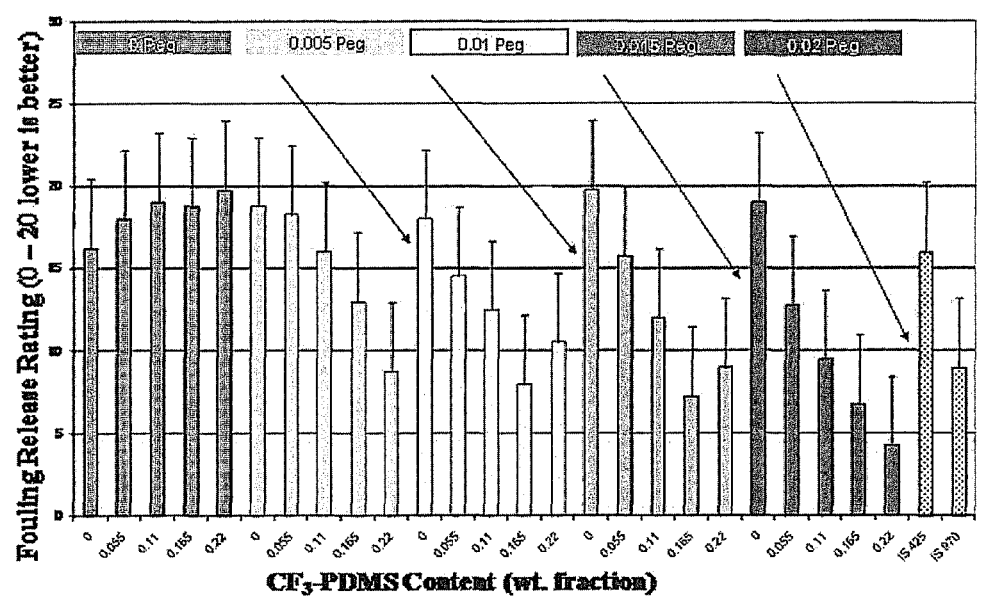
FIG. 2 shows fouling release data as a function of both $CF_3$-PDMS and TMS-PEG content.

FIG. 1 displays the general compositional space that is being investigated for the production of novel fouling-release coatings based the generation of amphiphilic surfaces. FIG. 2 shows fouling release data as a function of both $CF_3$-PDMS and TMS-PEG content. The fouling-release rating is the average rank obtained for 20 different coatings characterized using 4 different fouling-release measurements each based on a different organism. Thus, the lower the fouling-release rating, the better the overall fouling-release performance. As shown in FIG. 2, initial laboratory experiments showed a synergist effect between the silanol-terminated, fluorine-containing siloxane ($CF_3$-PDMS) and the trimethoxysilane-functional PEG (TMS-PEG) on fouling-release properties. As a result, a follow-up experiment was conducted that focused on higher levels of $CF_3$-PDMS and two levels of TMS-PEG.

Figure 3:
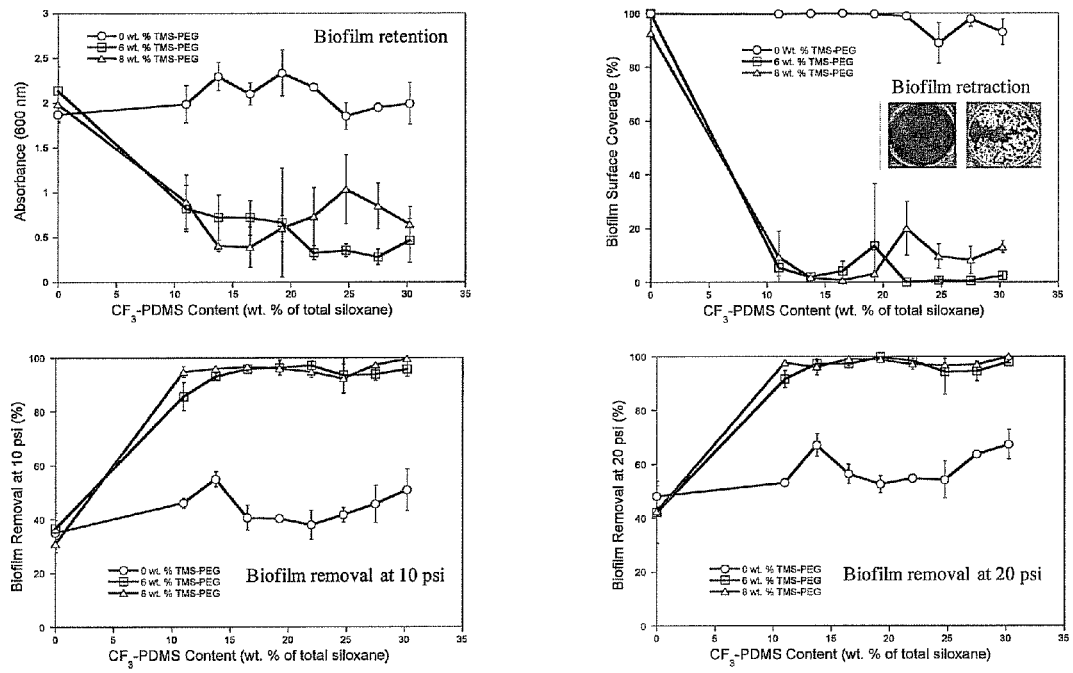
FIG. 3 shows biofilm retention, retraction, and removal data obtained using high-throughput assays and *C. lytica*.
Figure 4:
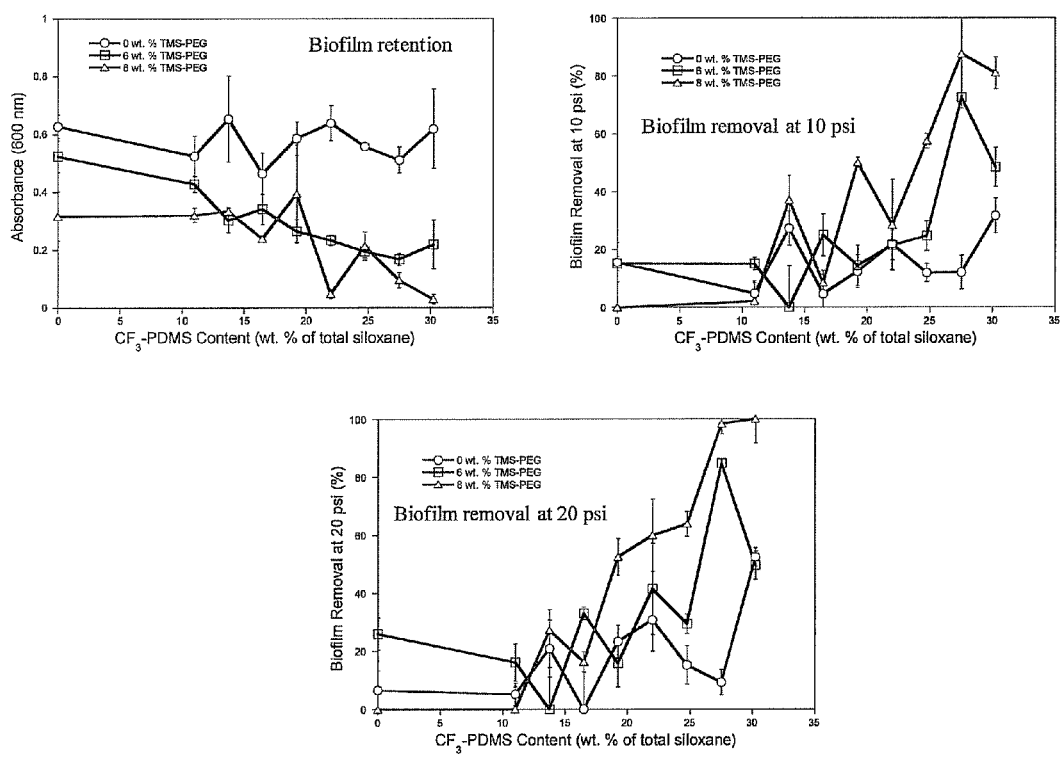
FIG. 4 shows biofilm retention and removal data obtained using high-throughput assays and *H. pacifica*.

FIGS. 3 and 4 exhibit fouling-release data obtained using two different marine bacteria, namely, *C. lytica* and *H. pacifica*, respectively. For *C. lytica* (FIG. 3), a dramatic synergy between the presence of $CF_3$-PDMS and TMS-PEG can be easily seen. For example, without the presence of $CF_3$-PDMS, there was essentially no significant difference in biofilm retention, biofilm retraction, and biofilm removal as a function of TMS-PEG content. However, replacement of just 10 weight percent of the silanol terminated PDMS with $CF_3$-PDMS in coatings containing TMS-PEG resulted in a dramatic reduction in biofilm retention and biofilm surface coverage and a major increase in biofilm removal.

For *H. pacifica* (FIG. 4), the addition of TMS-PEG to PDMS-based coatings (i.e. no $CF_3$-PDMS) resulted in a significant reduction in biofilm retention. Partial substitution of silanol-terminated PDMS with $CF_3$-PDMS resulted in a further decrease in biofilm retention with increasing $CF_3$-PDMS content.

With regard to biofilm removal, a dramatic increase in biofilm removal was achieved by increasing $CF_3$-PDMS content in coatings containing PEG modification. For example, the coating based on 8 wt. % TMS-PEG and no $CF_3$-PDMS showed no biofilm removal at a pressure of 20 psi; however, when 30 wt. % of the silanol-terminated PDMS was replaced by $CF_3$-PDMS in this composition, complete removal of the biofilm was obtained.

Figure 5:
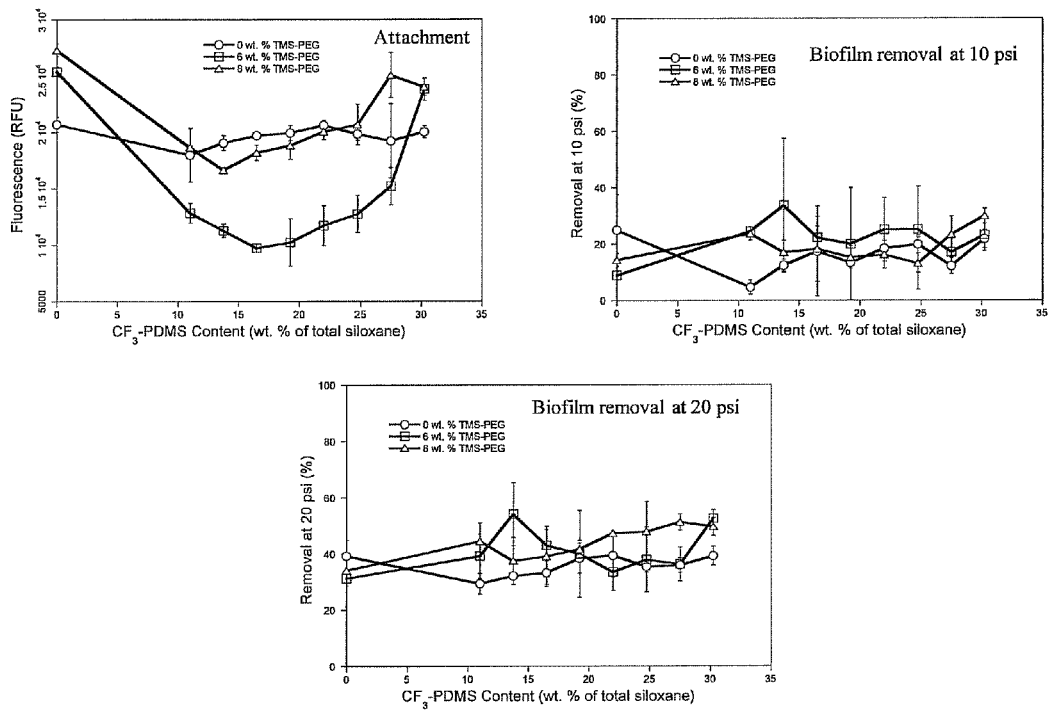
FIG. 5 shows cell attachment and removal obtained using high-throughput methods and *N. incerta*.

FIG. 5 exhibits data obtained the marine algae, *N. incerta*. For this microorganism, cell attachment exhibited a minimum at compositions possessing the low level of TMS-PEG (i.e. 6 wt. %) a $CF_3$-PDMS content of 17 wt. % based on total siloxane. With regard to removal, all the coatings exhibited very similar performance.

Barnacle adhesion strength was assessed using the barnacle reattachment assay. As shown in FIG. 6 and determined using statistical analysis, the incorporation of PEG moieties as well as $CF_3$-PDMS decreased barnacle adhesion strength. In addition, a synergist interaction between TMS-PEG and $CF_3$-PDMS was observed. As shown in FIG. 6 (right), a correlation was observed between the number of barnacles that would not attach and coating composition. For the assay, 10 barnacles were used for assessing adhesion strength. As shown in FIG. 6 (right), coatings possessing relatively high levels of $CF_3$-PDMS and TMS-PEG inhibited barnacle attachment. In addition, as illustrated in FIG. 7, barnacles removed from the coatings possessing relatively high levels of $CF_3$-PDMS and TMS-PEG showed "cupped" or "domed" base-plate morphology that was not observed for barnacles attached to the pure PDMS-based coating or a commercial fouling-release coating (Intersleek 970).

To illustrate the overall fouling-release performance of the coatings, the coatings were ranked from 1 to 27, with 1 being the best performing coating and 27 being the worst, for each fouling-release measurement made. For each coating, the rank values were averaged and are plotted in FIG. 8. From FIG. 8, the synergist interaction between TMS-PEG and $CF_3$-PDMS on fouling-release properties can be very easily observed.

In addition to the experimental coatings, the commercial fouling-release coating, Intersleek 970, was included in the experiment. FIG. 9 provides a comparison of the experimental coating derived from the highest TMS-PEG and $CF_3$-PDMS content to Intersleek 970. The spider plot shown in FIG. 9 was generated by normalizing all the data so that the value pertaining to the best performing coating of the two would be given the value of 1.0 and the value of the other coating would be expressed as a fraction of the value of the former. In addition, reattached barnacle adhesion was inversely transformed (1/value) so that higher values indicate lower adhesion strength. By expressing the data in this fashion, a larger area enclosed within the spider plot indicates better overall fouling release performance. From FIG. 9, it can be seen that the experimental coating was similar in performance to IS 970 with regard to bacterial biofilm removal and barnacle removal, but significantly better with respect to diatom removal.

Example III

Polysiloxane Coatings Containing Fluorinated Siloxane Segments

Amphiphilicity can be incorporated into polysiloxanes using both commercially-available starting materials as well as synthetically produced polysiloxane oligomers. FIGS. 10 to 12 display the synthetic schemes that can be carried out. The synthetic schemes shown in FIGS. 10 and 11 are completely based on commercially-available starting materials, while the synthetic scheme shown in FIG. 12 requires both monomer synthesis and ring-opening polymerization to produce oligomers for coating preparation.

FIG. 10 shows an illustrative synthetic scheme for generating amphiphilic polysiloxane coatings using commercially available starting materials and an addition-cure mechanism. The vinyl and hydride functionalities can be on any of the starting materials; only one representative reaction is shown.

FIG. 11 shows a synthetic scheme for generating amphiphilic polysiloxane coatings using commercially available starting materials and a moisture-cure mechanism. Hydrophilic groups are incorporated via the trimethoxysilane crosslinker.

FIG. 12 shows a synthetic scheme for generating amphiphilic polysiloxane coatings using hydrosilylation reaction to generate a functionalized cyclic siloxane, an anionic ring-opening mini-emulsion polymerization to produce novel silanol-terminated amphiphilic polysiloxanes, and production of coatings using the silanol-terminated amphiphilic polysiloxanes using a moisture-cure mechanism.

It should be understood that any and all features of the invention recited herein, including but not limited to various individual components of the polymer reaction mixture, various parameters concerning structure, methods of use, and the like, whether or not said components or features are recited together in the context of one embodiment or recited in different passages herein with respect to different embodiments, can be combined together in any combination to form the novel compositions or methods as envisioned by the invention.

Moreover, the complete disclosures of all patents, patent applications including provisional patent applications, and publications, and electronically available material cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. An amphiphilic polymeric material formed by reacting a mixture comprising at least one silane-functional hydrophilic component and at least one fluorine-containing silanol-terminated polysiloxane.

2. A substrate comprising a surface comprising a fouling-release coating, wherein the coating comprises the polymeric material of claim 1.

3. A maritime vessel comprising a polymeric coating comprising the polymeric material of claim 1.

4. The polymeric material of claim 1 wherein the silane-functional hydrophilic component comprises a silane-functional polyalkyleneglycol.

5. The polymeric material of claim 1 wherein the mixture further comprises a silane-functional fluorine-containing compound.

6. The polymeric material of claim 1 wherein the silane-functional hydrophilic component comprises an alkoxysilane.

7. The polymeric material of claim 1 wherein the fluorine-containing silanol-terminated polysiloxane comprises a copolymer of fluorine-containing monomers and non-fluorine-containing monomers.

8. The polymeric material of claim 1 wherein the mixture further comprises a non-fluorine-containing silanol-terminated polysiloxane.

9. The polymeric material of claim 8 wherein the silanol-terminated polysiloxane comprises a homopolymer, a heteropolymer, or a copolymer.

10. The polymeric material of claim 9 wherein the copolymer comprises a block copolymer or random copolymer.

11. The polymeric material of claim 8 wherein the silanol-terminated polysiloxane further comprises a hydrophilic component.

12. The polymeric material of claim 11 wherein the polysiloxane comprises a copolymer.

13. The polymeric material of claim 8 wherein the silanol-terminated polysiloxane comprises silanol-terminated polydimethylsiloxane.

14. The polymeric material of claim 1 which does not comprise silicone oil.

15. A method for making the polymeric material of claim 1 comprising reacting at least one silane-functional hydrophilic component with at least one fluorine-containing silanol-terminated polysiloxane under conditions to yield a polymeric material.

16. The method of claim 15 further comprising reacting a non-fluorine-containing silanol-terminated polysiloxane with the at least one silane-functional hydrophilic component and the at least one fluorine-containing silanol-terminated polysiloxane.

17. A method for making an amphiphilic polymeric material comprising reacting at least one vinyl functionalized fluorine-containing polysiloxane, at least one vinyl functionalized hydrophilic component, and at least one hydride functionalized polysiloxane, under conditions to yield a polymeric material.

18. A method for making a silanol-terminated polysiloxane comprising subjecting a cyclic siloxane to anionic ring-opening miniemulsion polymerization under conditions to yield a silanol-terminated polysiloxane.

19. The method of claim 18 wherein the silanol-terminated polysiloxane comprises an amphiphilic copolymer comprising at least one hydrophilic group at least one fluorine-containing group.

20. A polymeric material formed by reacting the amphiphilic silanol-terminated polysiloxane produced by the method of claim 19 with polydimethylsiloxane.

21. A method of protecting the surface of a substrate comprising coating the substrate surface with the polymeric material of claim 1.

22. A method of facilitating the removal of a biofilm or marine organism from a substrate surface comprising coating the surface with a polymeric material of claim 1.

\* \* \* \* \*